US012673028B2

(12) United States Patent    (10) Patent No.: US 12,673,028 B2
Caillaud et al.                  (45) Date of Patent: Jul. 7, 2026

(54) THERAPEUTIC POTENTIAL OF CELLULOSE-CYCLODEXTRIN-CURCUMIN NANOCRYSTALS IN THE TREATMENT OF PERIPHERAL NEUROPATHIES

(71) Applicant: UNIVERSITÉ DE LIMOGES, Limoges Cedex (FR)

(72) Inventors: Martial Caillaud, Limoges Cedex (FR); Alexis Desmoulière, Limoges Cedex (FR); Fabrice Billet, Limoges Cedex (FR); Franck Sturtz, Limoges Cedex (FR); Gautier Marck Arthur Ndong-Ntoutoume, Limoges Cedex (FR); Vincent Sol, Limoges Cedex (FR); Robert Granet, Limoges Cedex (FR)

(73) Assignee: UNIVERSITE DE LIMOGES, Limoges (FR)

( * ) Notice: Subject to any disclaimer, the term of this patent is extended or adjusted under 35 U.S.C. 154(b) by 788 days.

(21) Appl. No.: 17/626,247

(22) PCT Filed: Jul. 10, 2020

(86) PCT No.: PCT/IB2020/056505
§ 371 (c)(1),
(2) Date: Jan. 11, 2022

(87) PCT Pub. No.: WO2021/009640
PCT Pub. Date: Jan. 21, 2021

(65) Prior Publication Data
US 2022/0249391 A1    Aug. 11, 2022

(30) Foreign Application Priority Data
Jul. 12, 2019    (FR) ..................................... 1907897

(51) Int. Cl.
*A61K 9/51* (2006.01)
*A61K 9/00* (2006.01)
*A61K 9/06* (2006.01)
*A61K 31/12* (2006.01)
*B82Y 5/00* (2011.01)

(52) U.S. Cl.
CPC ............ *A61K 9/5161* (2013.01); *A61K 31/12* (2013.01); *A61K 9/0024* (2013.01); *A61K 9/06* (2013.01); *B82Y 5/00* (2013.01)

(58) Field of Classification Search
CPC ........ A61K 9/5161; A61K 31/12; A61P 25/02
See application file for complete search history.

(56) References Cited

U.S. PATENT DOCUMENTS

2018/0256509 A1* 9/2018 Friedman ............... A61K 33/04

FOREIGN PATENT DOCUMENTS

WO    WO-2016145219 A1 *  9/2016 ............. A61K 31/52

OTHER PUBLICATIONS

Ntoutoume et al., "Development of curcumin-cyclodextrin/cellulose nanocrystals complexes: New anticancer drug delivery systems", Feb. 1, 2016, Bioorganic & Medicinal Chemistry Letters, vol. 26, Issue 3, pp. 941-945. (Year: 2016).*
Search Report and Written Opinion issued in International Patent Application No. PCT/IB2020/056505 dated Oct. 15, 2020 (with English translation).
Sherer, "2018 Peripheral Nerve Society Annual Meeting Jul. 21-25, 2018 Baltimore, Maryland", Journal of the Peripheral Nervous System, vol. 23, No. 4, Dec. 1, 2018 (Dec. 1, 2018), p. 249-405, XP055676584.
Agthong, S., Kaewsema, A., Charoensub, T., "Curcumin Ameliorates Functional and Structural Abnormalities in Cisplatin-induced Neuropathy", Exp. Neurobiol., 2015, vol. 24, pp. 139-145.
Al Moundhri, M.S., Al-Salam, S., Al Mahrouqee, A., Beegam, S., Ali, B.H., "The Effect of Curcumin on Oxaliplatin and Cisplatin Neurotoxicity in Rats: Some Behavioral, Biochemical, and Histopathological Studies", J. Med. Toxicol., Off. J. Am. Coll. Med. Toxicol., 2013, vol. 9, pp. 25-33.
Caillaud M., Chantemargue B., Richard L., Vignaud L., Favreau F., Faye P.-A., et al., "Local low dose curcumin treatment improves functional recovery and remyelination in a rat model of sciatic nerve crush through inhibition of oxidative stress", Neuropharmacology, 2018, vol. 139, pp. 98-116.
Chahbouni M., López M.D.S., Molina-Carballo A., de Haro T., Muñoz-Hoyos A., Fernandez-Ortiz M., et al., "Melatonin Treatment Reduces Oxidative Damage and Normalizes Plasma Pro-Inflammatory Cytokines in Patients Suffering from Charcot-Marie-Tooth Neuropathy: A Pilot Study in Three Children", Mol., Basel Switz., 2017, vol. 22(10), 1728, pp. 1-14.
Daugherty, D.J., Marquez, A., Calcutt, N.A., Schubert, D., "A novel curcumin derivative for the treatment of diabetic neuropathy", Neuropharmacology, 2018, vol. 129, pp. 1-17.
Han, F., Luo, B., Shi, R., Han, C., Zhang, Z., Xiong, J., Jiang, M., Zhang, Z., "Curcumin Ameliorates Rat Experimental Autoimmune Neuritis", J. Neurosci. Res., 2014, vol. 92, pp. 743-750.
Kandhare, A.D., Raygude, K.S., Ghosh, P., Ghule, A.E., Bodhankar, S.L., "Therapeutic role of curcumin in prevention of biochemical and behavioral aberration induced by alcoholic neuropathy in laboratory animals", Neurosci. Lett., 2012, vol. 511, pp. 18-22.

(Continued)

*Primary Examiner* — Michael B. Pallay
(74) *Attorney, Agent, or Firm* — NIXON & VANDERHYE

(57)    ABSTRACT

Disclosed is a complex including: cellulose nanocrystals; at least one β-cyclodextrin molecule; and at least one curcumin molecule, suitable for use in the treatment of any kind of peripheral neuropathies. Further disclosed is a pharmaceutical composition including at least the complex and at least one pharmaceutically acceptable excipient. Also disclosed is the use of the complex or the pharmaceutical composition, in particular in the form of a hydrogel, a subcutaneous implant, an implantable pump, an implanted biofunctionalized nerve conduit, to improve the treatment compliance, to allow an extended release of the complex and to obtain better pharmacokinetics.

9 Claims, 16 Drawing Sheets

(56)         References Cited

OTHER PUBLICATIONS

Kaur, M., Singh, A., Kumar, B., Singh, S.K., Bhatia, A., Gulati, M., Prakash, T., Bawa, P., Malik, A.H., "Protective effect of co-administration of curcumin and sildenafil in alcohol induced neuropathy in rats", Eur. J. Pharmacol., 2017, vol. 805, pp. 58-66.

Khajavi M., Inoue K., Wiszniewski W., Ohyama T., Snipes G.J., Lupski J.R., "Curcumin Treatment Abrogates Endoplasmic Reticulum Retention and Aggregation-Induced Apoptosis Associated with Neuropathy-Causing Myelin Protein Zero-Truncating Mutants", Am. J. Hum. Genet., 2005, vol. 77, pp. 841-850.

Khajavi M., Shiga K., Wiszniewski W., He F., Shaw C.A., Yan J., et al., Oral Curcumin Mitigates the Clinical and Neuropathologic Phenotype of the Trembler-J Mouse: A Potential Therapy for Inherited Neuropathy, Am. J. Hum. Genet., 2007, vol. 81, pp. 438-453.

Liu, G.-M., Xu, K., Li, J., Luo, Y.-G., "Curcumin upregulates S100 expression and improves regeneration of the sciatic herve following its complete amputation in mice", Neural Regen. Res., 2016, vol. 11, pp. 1304-1311.

Lv, J., Cao, L., Zhang, R., Bai, F., Wei, P., "A curcumin derivative J147 ameliorates diabetic peripheral neuropathy in streptozotocin (STZ)-induced DPN rat models through negative regulation AMPK on TRPA1", Acta Cir. Bras., 2018, vol. 33, pp. 533-541.

Mohammadi, R., Mahmoodi, H., "Improvement of peripheral nerve regeneration following nerve repair by silicone tube filled with curcumin: a preliminary study in the rat model", Int. J. Surg., Lond. Engl., 2013, vol. 11, pp. 819-825.

Ndong Ntoutoume G.M.A., Granet R., Mbakidi J.P., Brégier F., Léger D.Y., Fidanzi-Dugas C., et al., "Development of curcumin-cyclodextrin/cellulose nanocrystals complexes: New anticancer drug delivery systems", Bioorg. Med. Chem. Lett., 2016, vol. 26, pp. 1-5.

Ndong Ntoutoume G.M.A., Grassot V., Brégier F., Chabanais J., Petit J.-M., Granet R., et al., "PEI-cellulose nanocrystal hybrids as efficient siRNA delivery agents-Synthesis, physicochemical characterization and in vitro evaluation", Carbohydr. Polym., 2017, vol. 164, pp. 258-267.

Nobbio L., Vigo T., Abbruzzese M., Levi G., Brancolini C., Mantero S., et al. "Impairment of PMP22 transgenic Schwann cells differentiation in culture: implications for Charcot-Marie-Tooth type 1A disease", Neurobiol. Dis., 2004, vol. 16, pp. 263-273.

Okamoto Y., Pehlivan D., Wiszniewski W., Beck C.R., Snipes G.J., Lupski J.R., et al., "Curcumin facilitates a transitory cellular stress response in Trembler-J mice", Hum. Mol. Genet., 2013, vol. 22, pp. 4698-4705.

Prasad, S., Tyagi, A.K., Aggarwal, B.B. "Recent Developments in Delivery, Bioavailability, Absorption and Metabolism of Curcumin: the Golden Pigment from Golden Spice", Cancer Res. Treat., Off. J. Korean Cancer Assoc., 2014, vol. 46, pp. 2-18.

Sereda M., Griffiths I., Puhlhofer A., Stewart H., Rossner M.J., Zimmerman F., et al., "A Transgenic Rat Model of Charcot-Marie-Tooth Disease", Neuron, 1996, vol. 16, pp. 1049-1060.

Sharma, R.A., Euden, S.A., Platton, S.L., Cooke, D.N., Shafayat, A., Hewitt, H.R., Marczylo, T.H., Morgan, B., Hemingway, D., Plummer, S.M., Pirmohamed, M., Gescher, A.J., Steward, W.P., "Phase I Clinical Trial of Oral Curcumin: Biomarkers of Systemic Activity and Compliance", Clin. Cancer Res., Off. J. Am. Assoc. Cancer Res., 2004, vol. 10, pp. 6847-6854.

Shoba, G., Joy, D., Joseph, T., Majeed, M., Rajendran, R., Srinivas, p. S., "Influence of Piperine on the Pharmacokinetics of Curcumin in Animals and Human Volunteers", Planta Med., 1998, vol. 64, pp. 353-356.

Wahlstrom, B. and Blennow, G., "A Study on the Fate of Curcumin in the Rat", Acta pharmacologica et toxicologica, 1978, vol. 43, Issue 2, pp. 86-92.

Yang, K.-Y., Lin, L.-C., Tseng, T.-Y., Wang, S.-C., Tsai, T.-H., "Oral bioavailability of curcumin in rat and the herbal analysis from Curcuma longa by LC-MS/MS", J. Chromatogr. B., Analyt. Technol. Biomed. Life. Sci., 2007, vol. 853, pp. 183-189.

Extended European Search Report, issued in European Patent Application No. 25159479.2 dated Jul. 18, 2025.

Sasaki et al., "Innovative Preparation of Curcumin for Improved Oral Bioavailability", Biological and Pharmaceutical Bulletin, vol. 34, No. 5, 2011, pp. 660-665.

Yavarpour-Bali et al., "Curcumin-loaded nanoparticles: a novel therapeutic strategy in treatment of central nervous system disorders", International Journal of Nanomedicine, 2019, vol. 14, pp. 4449-4460.

* cited by examiner

Creatine Phosphokinase

THERAPEUTIC POTENTIAL OF CELLULOSE-CYCLODEXTRIN-CURCUMIN NANOCRYSTALS IN THE TREATMENT OF PERIPHERAL NEUROPATHIES

CROSS-REFERENCE TO THE RELATED APPLICATIONS

This application is the U.S. national phase of International Application No. PCT/IB2020/056505 filed Jul. 10, 2020 which designated the U.S. and claims priority to FR Patent Application No. 1907897 filed Jul. 12, 2019, the entire contents of each of which are hereby incorporated by reference.

BACKGROUND OF THE INVENTION

Field of the Invention

The present invention relates to the field of treatment of any kind of peripheral neuropathies, in particular Charcot-Marie-Tooth disease type 1A.

Description of the Related Art

Peripheral nerves are subject to many pathologies and the etiology of peripheral neuropathies (PN) is wide: metabolic disorders, infections, toxins, physical injuries and genetic mutations, etc. Charcot-Marie-Tooth disease type 1A (CMT1A) is the most common inherited genetic peripheral neuropathy. It is characterized by an overexpression of the PMP22 protein involved in the maintenance of the myelin sheath.

Currently, there is no pharmacological treatment for this condition. It therefore seems urgent to develop multi-targeted molecules acting simultaneously on different physiopathological aspects.

Recently, interest in the role of dietary antioxidants, such as curcumin, has generated numerous studies. This molecule has long been used in Asian medicine for its therapeutic properties. However, it is not easily absorbed in the intestines and is quickly degraded due to a very fast metabolism. As a result, very high doses of curcumin are needed to obtain therapeutic effects without having the certainty that the curcumin reaches the target organ.

Curcumin is a polyphenol extracted from the root of *Curcuma longa*. This molecule has long been used in Asian medicine for its anti-inflammatory and antibacterial properties. One of the main obstacles to the use of curcumin in therapy is its very low bioavailability, as well as its very rapid metabolism. The bioavailability of a molecule is defined as the fraction of the administered dose or of the active ingredient released by the pharmaceutical form that reaches the systemic bloodstream unchanged and the speed at which this process is carried out. In the case of digestive absorption, curcumin is rapidly metabolized via conjugation mechanisms (to glucuronoconjugate and sulfate). These modifications are intended to make curcumin less lipophilic so that it can be eliminated more quickly by the body. The liver is the main organ where these conjugation reactions take place. Concomitantly to the conjugation and especially in the case of an intravenous administration, curcumin undergoes reactions by microsomal hepatic enzymes, the reductases. Metabolites are thus formed which are mainly reduced derivatives of curcumin: dihydrocurcumin, tetrahydrocurcumin, hexahydrocurcumin and hexahydrocurcuminol. These major metabolites then undergo conjugation reactions to be rapidly eliminated or excreted. The present inventors have developed an innovative compound based on cellulose-cyclodextrin-curcumin nanocrystals (CNCs-CD-Cur or Nano-Cur) to overcome this obstacle. This complex considerably improves the bioavailability of curcumin and thus reduces the dose required to produce therapeutic effects, particularly on peripheral neuropathies.

Until now, the main pharmacological approach used in the clinic for the management of peripheral neuropathies has been based on the use of analgesics and anti-inflammatory drugs. In situations where the nerve is partially or completely severed, surgical approaches of suturing or grafting of nerve conduits, bio-functionalized or not, are used. Nevertheless, the effectiveness of these therapeutic strategies remains limited and does not address the cause of the disease, but mainly the symptoms. This lack of pharmacological treatment is particularly dramatic in the case of hereditary genetic peripheral neuropathies, as they are diffuse and occur very early in the life of the patients.

The cellulose-cyclodextrin-curcumin nanocrystals developed by the present inventors constitute a new therapeutic approach to overcome the low bioavailability of curcumin and the absence of effective pharmacological treatment of peripheral neuropathies.

SUMMARY OF THE INVENTION

Charcot-Marie-Tooth (CMT) diseases are the most common forms of inherited peripheral motor and sensory neuropathies. Epidemiologically, the overall prevalence of CMTs is usually 1/2500. These neuropathies result from mutations in genes encoding proteins responsible for the maintenance of the myelin sheath and/or the axons themselves. CMT diseases are a condition characterized by extreme weakness and atrophy of the muscles of the legs and feet, gait abnormalities, loss of tendon reflexes, and numbness of the lower limbs. The CMT1A form affects about 30-40% of patients with CMT disease. In this neuropathy, there is a loss and/or malformation of the myelin sheath of peripheral nerve fibers, which may be characterized by a decrease in motor nerve conduction velocity of the upper limb nerves <33-38 m/s. Sensory symptoms are usually less prominent and may be subtle.

Curcumin has been shown in numerous studies to improve functional recovery in animal models of hereditary (Khajavi et al., 2005, Khajavi et al., 2007, Okamoto et al., 2013), autoimmune (Han et al., 2014), alcoholic (Kandhare et al., 2012, Kaur et al., 2017), diabetic (Lv et al., 2018, Daugherty et al., 2018), chemo-induced (Agthong et al., 2015, Al Moundhri et al., 2013), and traumatic neuropathies, including crush, chronic constriction, and complete nerve transection (Liu et al., 2016; Mohammadi and Mahmoodi, 2013). However, the doses used in these studies are very high, between 50 and 300 mg/kg/day.

Regarding the bioavailability of curcumin, an initial study was performed by Wahlstrom and Blennow in 1978, in which curcumin was administered to Sprague-Dawley rats at a dose of 1 g/kg. In this study, low levels of curcumin were observed in the plasma of the rats. Thus, later studies in rats determined that the oral bioavailability of curcumin is approximately 1% (Shoba et al., 1998, Yang et al., 2007). As a result, in humans, very high doses of curcumin (3.6 to 12 g) must be administered, but without obtaining very high plasma concentrations of curcumin (Sharma et al., 2004). It should be noted that no toxic effects have been reported in humans at these doses (Sharma et al., 2004).

The beneficial properties of curcumin are hampered by its low solubility (due to its hydrophobicity) and low bioavailability, combined with instability in solution that results in rapid elimination from the blood (Sharma et al., 2004).

In a previous study, the inventors showed in a rat model of traumatic sciatic nerve injury that a low dose of curcumin delivered locally and continuously promotes nerve repair and functional recovery (Caillaud et al., 2018).

Nano-technological approaches have been developed, including incorporation or encapsulation of curcumin into liposomes, polymeric micelles, polymeric nanoparticles, nanogels, nanoemulsions, inclusion complexes, solid lipid nanoparticles, dendrimers, phytosomes, mesoporous silica nanoparticles, or metal nanoparticles (Prasad et al., 2014). All of these nanovectors were able to increase the bioavailability and beneficial effects of curcumin.

In contrast, none of these curcumin-associated nanovectors have been tested on peripheral neuropathies.

The inventors have developed nanobiomaterials capable of specifically delivering natural hydrophobic compounds such as chlorophyll derivatives or curcumin, but also siRNAs.

This new delivery system is composed of cellulose nanocrystals (CNCs) which benefit from a good mechanical resistance, a liquid crystalline character, a specifically high surface area, a good biocompatibility, biodegradability and durability. Obtained by acid hydrolysis of cotton fibers, these nanofibers are defined as elongated nanoparticles 100-200 nm long, 10-20 nm wide and 5-10 nm thick. The negative charges present on the surface of CNCs are used to form ionic complexes with cationic β-cyclodextrins (CDs), which are well known to form inclusion complexes with host molecules. The β-CD is the most commonly used, due to its relatively easy synthesis, its low cost and also to the large number of polar molecules that can fit into its internal cavity. CNCs were loaded with β-CD and then curcumin was incorporated into the β-CD to form curcumin-β-CD-CNCs nanocrystals (Ndong Ntoutoume et al., 2016). In vitro, these curcumin-β-CD-CNCs nanocrystals have improved the intracellular penetration of curcumin. However, the effects of these nanocrystals had not, until now, been tested in vivo.

The present invention relates to a complex comprising:
  cellulose nanocrystals;
  at least one molecule of β-cyclodextrin;
  at least one curcumin molecule,
for use in the treatment of any kind of peripheral neuropathies.

The synthesis of the complex will be detailed below with reference to the attached figures. Briefly, the cellulose nanocrystals were obtained from an acid hydrolysis of cotton fiber cellulose. Curcumin was extracted from curcuminoid powder and β-cyclodextrins were attached to the cellulose nanocrystals by reaction with glycidyltrimethylammonium chloride. Finally, curcumin was incorporated into the β-cyclodextrins in order to obtain the complex of the invention.

In one embodiment, the peripheral neuropathy may be Charcot-Marie-Tooth disease. Charcot-Marie-Tooth (CMT) diseases are the most common forms of inherited peripheral motor and sensory neuropathies. These neuropathies result from mutations in genes encoding proteins responsible for the maintenance of the myelin sheath and/or the axons themselves.

In one particular embodiment, the peripheral neuropathy may be Charcot-Marie-Tooth disease type 1A. Charcot-Marie-Tooth disease 1A (CMT1A) is the most common inherited genetic peripheral neuropathy. It is characterized by an overexpression of the PMP22 protein involved in the maintenance of the myelin sheath.

In another embodiment, the peripheral neuropathy can be related to a traumatic injury.

Indeed, the injury to a peripheral nerve may be secondary to a trauma or a compression of that nerve.

According to one aspect, the complex is intended to be administered to a subject in a therapeutically effective amount.

The term "therapeutically effective amount" means the rate or amount of compound necessary and sufficient to slow or stop the progression, worsening, or deterioration of one or more symptoms of peripheral neuropathy, in particular Charcot-Marie-Tooth disease or a peripheral neuropathy of traumatic origin, and to alleviate the symptoms of the disease.

The "therapeutically effective amount" depends on the subject, the stage of the disease to be treated and the method of administration, and can be determined by routine operations by the person skilled in the art. This amount may vary with the age and gender of the subject.

In addition, the specific therapeutically effective amount for any subject will depend on a variety of factors including the disorder being treated and the severity of the disorder; the potency of the specific compound used; the specific composition used, the age, body mass, general health, gender and diet of the subject; the duration of administration, the route of administration of the specific compound used; the duration of treatment; the drugs used in combination or simultaneously with the specific compound used; and similar factors well known in the medical art.

For example, it is well within the competence of the person skilled in the art to begin with doses of the compound at rates lower than those required to achieve the desired therapeutic effect and to gradually increase the dosage until the desired effect is achieved.

In a particular embodiment, the therapeutically effective amount may be between 0.02 and 200 mg/kg/day of curcumin, in particular between 0.1 and 1 mg/kg/day, more particularly between 0.1 and 0.3 mg/kg/day.

More particularly, the therapeutically effective amount may be 0.2 mg/kg/day of curcumin.

According to another aspect, the complex is intended to be administered to a subject by an injectable route, preferably by a subcutaneous, intramuscular, intravenous or perineural route, orally, transdermally or in an implanted biofunctionalized nerve conduit.

Examples of forms suitable for injection include, but are not limited to, solutions, such as, for example, sterile aqueous solutions, dispersions, emulsions, suspensions, solid forms suitable for use in preparing solutions or suspensions by the addition of a liquid prior to use, e.g., a powder, liposomal forms or the like.

The mode of administration can therefore also be by injection or by gradual infusion. Injection may be intravenous, intraperitoneal, intramuscular, subcutaneous or transdermal. Preparations for parenteral administration may include sterile aqueous or non-aqueous solutions, suspensions or emulsions. Examples of non-aqueous solvents are benzyl alcohol, ethanol, propylene glycol, polyethylene glycol, vegetable oils or injectable organic esters such as ethyl oleate. Aqueous vehicles include water, alcohol/water solutions, emulsions or suspensions.

Also, examples of forms suitable for oral administration include, but are not limited to, tablets, orodispersion tablets, effervescent tablets, powders, granules, pills (including sweetened pills), dragees, capsules (including soft gelatin capsules), syrups, liquids, gels or other solutions, suspensions, slurries, liposomal forms and the like.

Furthermore, "implanted biofunctionalized nerve conduit" means an artificial nerve prosthesis for the repair and regeneration of peripheral nerves in the form of guide tubes. These tubes can be used for the administration of the complex of the present invention.

In another embodiment, the invention relates to a pharmaceutical composition comprising:
 at least the complex of the invention;
 at least one pharmaceutically acceptable excipient.

The term "pharmaceutically acceptable excipient" refers to a non-toxic material that is compatible with a biological system such as a cell, cell culture, tissue or organism. This pharmaceutically acceptable excipient does not produce any adverse, allergic or other reaction when administered to an animal, particularly a human being. The characteristics of the excipient will depend on the mode of administration used.

This includes any solvent, diluent, dispersion medium, agglutinating agent, binder, lubricant, disintegrant, coating, antibacterial and antifungal agent, isotonic agent and absorption retardant agent, and similar adjuvants. A pharmaceutically acceptable excipient refers to a non-toxic solid, semi-solid or liquid filler, a diluent, an encapsulating material or an ancillary formulation of any type. For human administration, the preparations shall meet the requirements of sterility, pyrogenicity, general safety and purity as required by Good Manufacturing Practices for active substances for human and veterinary use.

In a particular embodiment, the pharmaceutical composition is intended to be administered to a subject in a therapeutically effective amount.

In the pharmaceutical composition of the present invention, the complex, alone or in combination with an excipient, may be administered in a unitary form of administration, as a mixture with conventional pharmaceutical carriers, to animals and humans. Suitable unit dosage forms include those suitable for oral administration such as tablets, capsules, powders, granules and oral suspensions or solutions, sublingual and buccal forms of administration, aerosols, implants, subcutaneous, transdermal, topical, intraperitoneal, intramuscular, intravenous, subdermal, intrathecal and intranasal forms of administration and rectal forms of administration.

In another embodiment, the invention relates to the use of the complex or the pharmaceutical composition, in the form in particular of a hydrogel, a subcutaneous implant, an implantable pump, an implanted biofunctionalized nerve conduit, to improve the treatment compliance, to allow an extended release of the complex and to obtain better pharmacokinetics.

Indeed, the use of the complex of the present invention, through the significant improvement of the bioavailability of curcumin in its complexed form, allows an extended duration of release of the complex comprising curcumin. This contributes to facilitate the compliance of the subject with the treatment, which becomes less restrictive, with administrations more spaced out in time in comparison with a treatment with curcumin alone.

BRIEF DESCRIPTION OF THE DRAWINGS

To better illustrate the object of the present invention, the following examples will now be described below, by way of illustration and not limitation, in connection with the appended drawings:

FIG. 3C: graphical representation of creatinine dosage as a marker of muscle lysis.

DESCRIPTION OF THE PREFERRED EMBODIMENTS

Figure 1A:
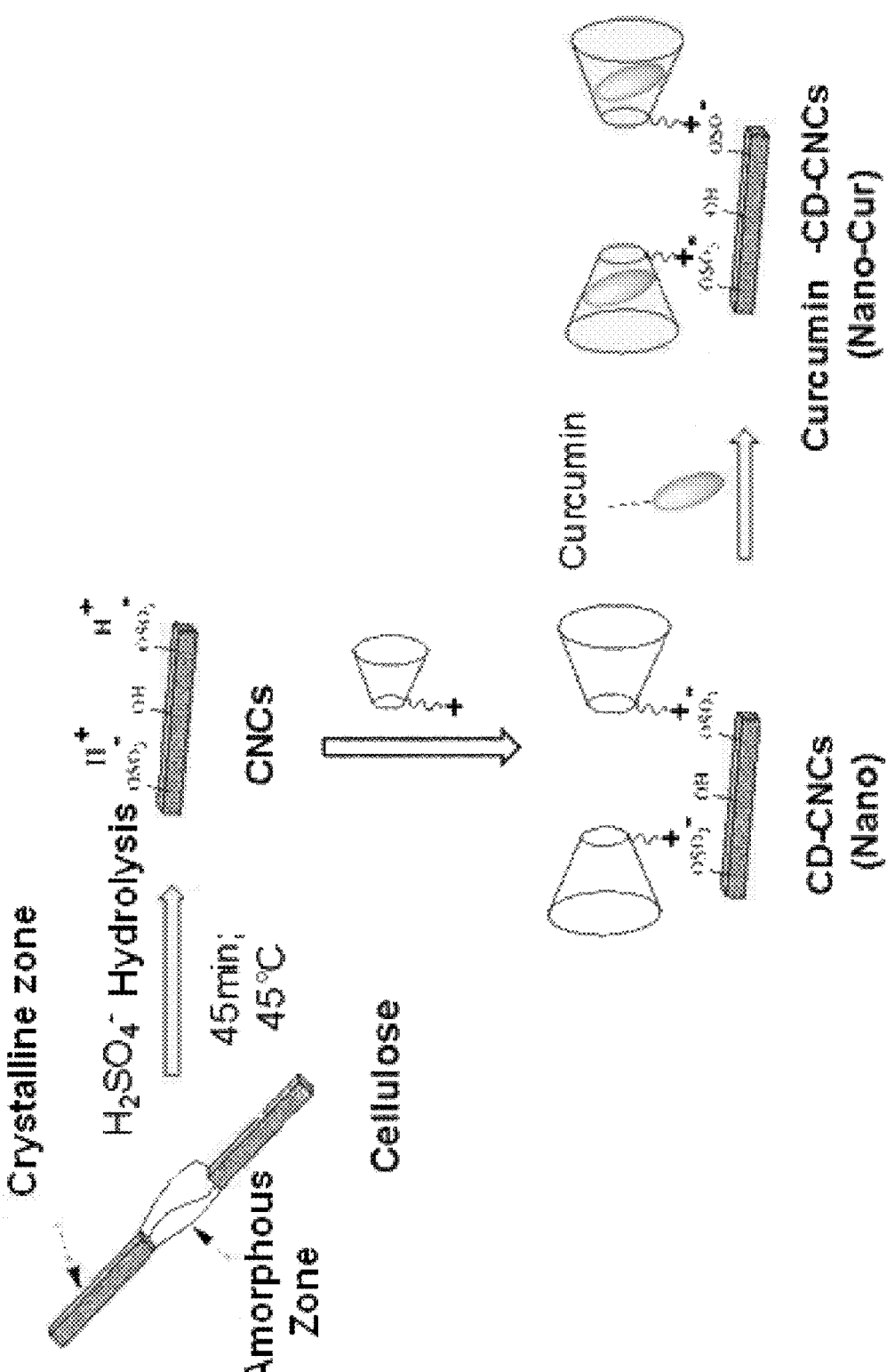
FIG. 1A: schematic diagram of the synthesis of curcumin-$\beta$-cyclodextrin-cellulose nanocrystals (Nano-Cur).

The following examples illustrate the invention.

Materials and Methods

Synthesis of Cellulose-Cyclodextrin-Curcumin Nanocrystals (CNCs-CD-Cur or Nano-Cur)

Acid hydrolysis ($H_2SO_4$) of cotton fibers yielded negatively charged cellulose nanocrystals (CNCs). Cationic cyclodextrin (CD) was prepared by reaction of β-cyclodextrin (β-CD) with glycidyltrimethylammonium chloride and then attached by ionic interaction to the CNCs in order to form the CNCs-CD complex (Nano). In parallel, curcumin was extracted from curcuminoid (turmeric) powder and then encapsulated in the CDs in order to obtain the curcumin-CD-CNCs complexes (CNCs-CD-Cur or Nano-Cur).

Animals

The experiments were performed on 60 one-month-old male rats (30 CMT1A heterozygous rats and 30 wild type Sprague Dawley rats). The generation of CMT1A (PMP22 transgenic) rats is described in Sereda et al. (1996).

The experimental protocols were specifically approved by the Regional Animal Experimentation Ethics Committee (CREEAL n° 16-2013-16, APAFIS #18160-2018122015432214 v1).

Treatment of Rats

CMT1A transgenic rats (1-month-old males) were treated with the cellulose-cyclodextrin-curcumin nanocrystals (Nano-Cur) daily by intraperitoneal injection of 0.2 mg/kg/day curcumin for 8 weeks.

Rats were randomized into 6 groups: WT wild type rats treated with saline solution (WT/saline solution, n=10), WT rats treated with cellulose-cyclodextrin nanocrystals (Nano) solubilized in saline solution (WT/Nano, n=10), WT rats treated with Nano-Cur solubilized in saline solution (WT/Nano-Cur, n=10), CMT1A rats treated with saline solution (CMT1A/saline solution, n=10), CMT1A rats treated with Nano solubilized in saline solution (CMT1A/Nano, n=10) and CMT1A rats treated with Nano-Cur solubilized in saline solution (CMT1A/Nano-Cur, n=10).

Behavioral Tests

Thermal Sensitivity

Withdrawal latencies following a thermal stimulus were measured using a 52° C. hot plate (Bioseb, France) weekly for 8 weeks. After 10 minutes of acclimation, animals were placed on the hot plate until the expression of nociceptive behaviors such as hind leg shaking or animal jumping. The maximum test duration was set at 30 seconds to avoid tissue damage. Three separate tests, each for 10 minutes, were performed and the mean value was used to represent the thermal nociception threshold for each animal.

Mechanical Sensitivity

The threshold for hind paw withdrawal in response to a mechanical stimulus was measured weekly for 8 weeks using a series of von Frey filaments (Bio-VF-M, Bioseb, France).

Grip Test

Gripping strength tests were performed weekly for 8 weeks with the T-bar of a gripping strength measuring device (BIO-GS3, Bioseb, France).

Balance Test

The balance test on an elevated bar was used to evaluate the muscular strength of the four legs and the steady-state balance performance of the animals. This test was performed weekly for 8 weeks. The rat was placed on its four legs in the middle of the wooden bar (diameter: 2.5 cm, length: 50 cm, height 30 cm). The time spent on the bar (latency to fall) in each trial was recorded. Three separate tests, each for 10 minutes, were performed and the average value of these tests was calculated to represent steady-state balance performance.

Electrophysiological Analysis

The M wave and H reflex were measured with the PowerLab/26T (ADInstruments, France) after supramaximal stimulation of the distal and proximal regions of the sciatic nerve. Motor nerve conduction velocity (MNCV) and sensitive nerve conduction velocity (SNCV) were calculated from M-wave and H-reflex latency, respectively.

Optic Microscopy and Morphometric Analysis

Sciatic nerve samples were fixed in 2.5% glutaraldehyde and embedded in epoxy resin (Euromedex, France). Semi-fine cross-sections (1.5 μm) were labeled with toluidine blue and used for morphometric assessments, which were performed in single blind. Tissue damage was estimated by the total number of myelinated axons per nerve section and the average diameter of nerve fibers. Myelin sheath thickness was calculated by the formula: (fiber diameter–axon diameter)/2. The degree of myelination (G-ratio) was estimated by the ratio of axon diameter to fiber diameter and the ratio of myelin thickness to axon diameter.

Immunohistochemistry

Sciatic nerve samples were embedded in OCT glue and frozen in liquid nitrogen. Cryostat sections (5 μm) were dried for 4 hours on Superfrost/+ slides, followed by fixation with 4% paraformaldehyde for 10 minutes at room temperature. Permeabilization of the sections was performed by incubation in 0.1% Tween20 in PBS for 15 minutes. Non-specific binding was blocked with 10% BSA in PBS for 1 hour. Anti-PMP22 primary antibody (SAB4502217-100UG, Sigma Aldrich, 1:200) was added in 4% BSA in PBS overnight at 4° C. Samples were then rinsed for 15 minutes in PBS at room temperature and then incubated with the secondary antibody (anti-rabbit made in donkey Alexa-fluor 594, Dako, 1:200) in 4% BSA in PBS for 2 hours at room temperature. The slides were mounted using Dako fluorescence mounting medium (Dako France S.A.S, France). Red fluorescence was visualized and intensity measured by fluorescence microscopy (Nikon H600L optical microscope) and images were captured using a Nikon digital camera (Nikon, France).

Western Blot

Proteins were separated by SDS-PAGE electrophoresis and then transferred to a cellulose membrane. Blots were incubated with mouse monoclonal primary antibodies recognizing either β-cytoplasmic actin, myelin protein zero (MPZ), myelin basic protein (MBP) or with rabbit polyclonal antibodies recognizing peripheral myelin protein 22 (PMP22) or type 2 nuclear factor (erythroid derivative) (Nrf2).

Histoenzymology of Gastrocnemius Muscle

Gastrocnemius muscle fragments were embedded in OCT glue, frozen in liquid nitrogen, and stored at –80° C. Cross-sections of muscle (5 μm) were made using a Leica CM 1850 UV cryostat at 25° C. and collected on glass slides. The sections were then stained using either the m-ATPase reaction with alkaline and acid preincubation, the method of Padykula and Herman (1955); the NADH-TR reaction according to the method of Pearse (1968) modified by Dobowitz and Brooke (1973) or the succinate dehydrogenase (COX-SDH) reaction described by Nachalas et al. (1957) and modified by Wegman and Tordet-Coidroit (1960). For each sample, images were acquired using a Nikon H600L optical microscope (Nikon, Japan) and were taken from 3 randomly selected fields.

Detection of Reactive Oxygen Species in Sciatic Nerves

Cryostat cross sections of sciatic nerves (5 μm) were washed with PBS and incubated with 5 μM CellROX-Green reagent (Life Technologies GmbH, Germany) for 30 minutes at 37° C. The nuclei were stained using DAPI. Reactive oxygen species (ROS) were assessed by fluorescence intensity using a fluorescence microscope.

Cell Culture and Assessment of Oxidative Stress In Vitro

Schwann Cell Culture

Schwann cells (SCs) were isolated from sciatic nerves of wild type (WT) male rats as well as 8-week-old CMT1A rats. SCs were cultured in SC culture medium (described in Caillaud et al., 2018): DMEM D-valine+2 mM glutamine (Gibco)+10% fetal calf serum (Gibco)+1% N2 supplement (Gibco)+20 μg/mL bovine pituitary extract+5 μM forskolin (Gibco)+100 U/mL penicillin/streptomycin (Gibco)+250 μg/mL fungizone (Gibco). SCs were identified using immunofluorescent labeling for S-100 protein.

In Vitro Oxidative Stress

Wild type SCs were pretreated with curcumin (0.001, 0.01, 0.1, 1, or 10 μM) (Sigma) or Nano-Cur (0.001, 0.01, 0.1, 1, or 10 μM) for 8 hours. To induce oxidative stress, SCs were subjected to $H_2O_2$ (0.1 mM) treatment for 8 hours. Total ROS and mitochondrial superoxide ions were assessed using the CellROX-Green reagent (Life Technologies GmbH) and the mitochondrial superoxide indicator Mito-SOX Red (Life Technologies GmbH), respectively, according to the manufacturer's recommendations. In addition, the effects of curcumin and Nano-Cur on ROS production were assessed by determination of mitochondrial membrane potential (Alp), which was performed by incubation with rhodamine 123 (Rho123) as previously described in Caillaud et al. (2018).

Myelination in Co-Cultures of Schwann Cells and Neurons

Co-cultures of sensory neurons (WT) and Schwann cells (CMT1A) were established using previously published methods (Nobbio et al., 2004). Briefly, co-cultures were maintained for 30 days in neurobasal medium (Invitrogen, Srl) supplemented with 15% fetal calf serum (NCS, Invitrogen, Srl) and 5 ng/mL NGF (Invitrogen, Srl). The co-cultures were treated for 1 week with 0.01 μM Nano-Cur. To assess changes in cell morphology and myelination, immunofluorescent labeling of MBP (myelin basic protein) and NFM (neurofilament M protein) was performed.

Statistical Analysis

All data are expressed as mean+/–standard error. If normality (Shapiro-Wilk test) and homogeneity of variances (Brown-Forsythe test) were observed, then the data were compared using either a one-factor or two-factor ANOVA with repeated measures, followed by a Tukey or Dunnett post-hoc comparison test. If normality and homogeneity of variances were not observed, then the data were compared using a Krustal-Wallis test followed by a Dunn's post-hoc test. All statistical analyses were performed with Graphpad statistical software (GraphPad Software, Inc., USA). Differences were considered significant when p was <0.05, <0.01 or <0.001.

Example 1: CNCs-CD-Curcumin Nanocrystals (Nano-Cur) Improve the Bioavailability of Curcumin In Vivo Referring to FIG. 1A, after acid hydrolysis ($H_2SO_4$) of cotton fibers, the resulting cellulose nanocrystals (CNCs) exhibit negative surface charges, giving them stability in aqueous solution. These CNCs are then functionalized with cationic cyclodextrins (CDs) obtained by reaction with glycidyltrimethylammonium chloride and β cyclodextrin. Finally, curcumin is encapsulated in the β CDs of the CNCs-CD complex (Nano).

Figure 1B:
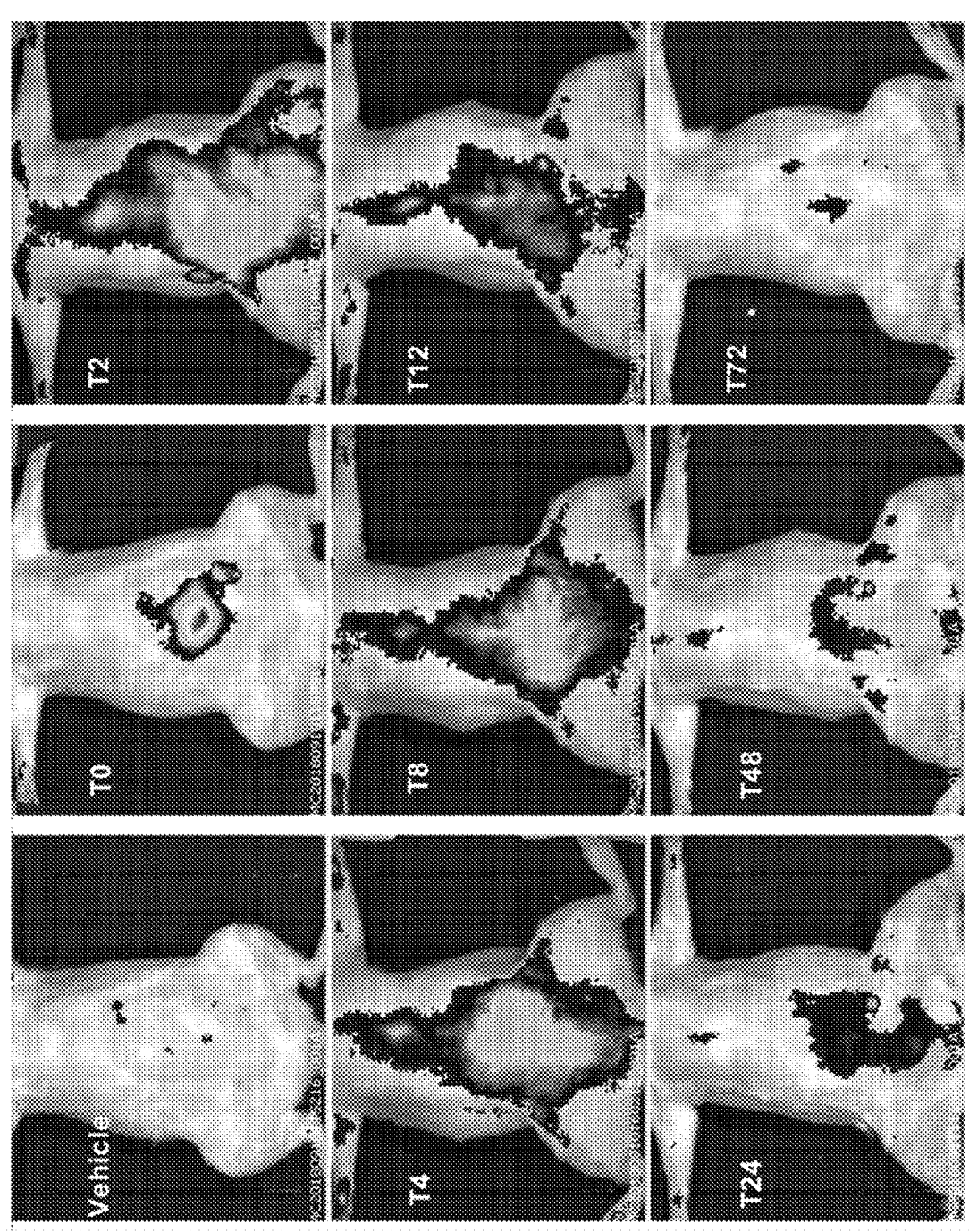
FIG. 1B: in vivo fluorescence imaging of the dispersion of cyclodextrin-cellulose nanocrystals (Nano) labeled with the fluorophore Dylight-800 in wild type rats (WT) at different post-injection times.

Injection of the CNCs-CD nanocrystals alone (Nano) labeled with the fluorophore Dylight 800 showed, by means of in vivo imaging, a dispersion of the CNCs-CD nanocrystals throughout the animal's body (FIG. 1B) and that these were detectable up to 72 hours after injection. Furthermore, the results presented in Table 1 below showed that curcumin nanocrystals (CNCs-CD-Curcumin or Nano-Cur) increased the bioavailability of curcumin by 250 times compared to the administration of curcumin alone, and maintained an extended release of curcumin in the plasma (at least 12 hours after administration).

TABLE 1

| Bioavailability of curcumin in plasma | | | | | | |
|---|---|---|---|---|---|---|
| | Curcumin 50 mg/kg | | | Nano-Cur 0.2 mg/kg | | |
| Time (hours) | Concentration (ng/mL) | SEM | Number | Concentration (ng/mL) | SEM | Number |
| 0 | 0 | ±0 | n = 3 | 0 | ±0 | n = 3 |
| 1 | 24.9 | ±0.2 | n = 3 | 26.3 | ±16.1 | n = 3 |
| 2 | 4.3 | ±0.7 | n = 3 | 5.3 | ±0.7 | n = 3 |
| 8 | 0 | ±0 | n = 3 | 15.4 | ±8.9 | n = 3 |
| 12 | 0 | ±0 | n = 3 | 10.8 | ±6.5 | n = 3 |

Example 2: Treatment with CNCs-CD-Curcumin Nanocrystals (Nano-Cur) Improves the Phenotype of CMT1A Rats Analyses performed using behavioral test data in all wild type (WT) groups indicated no significant differences between groups (WT/saline solution, WT/Nano, and WT/Nano-Cur) during the 8 weeks of testing. In addition, no significant differences were observed between the CMT1A/saline solution and CMT1A/Nano groups.

Figure 2A:
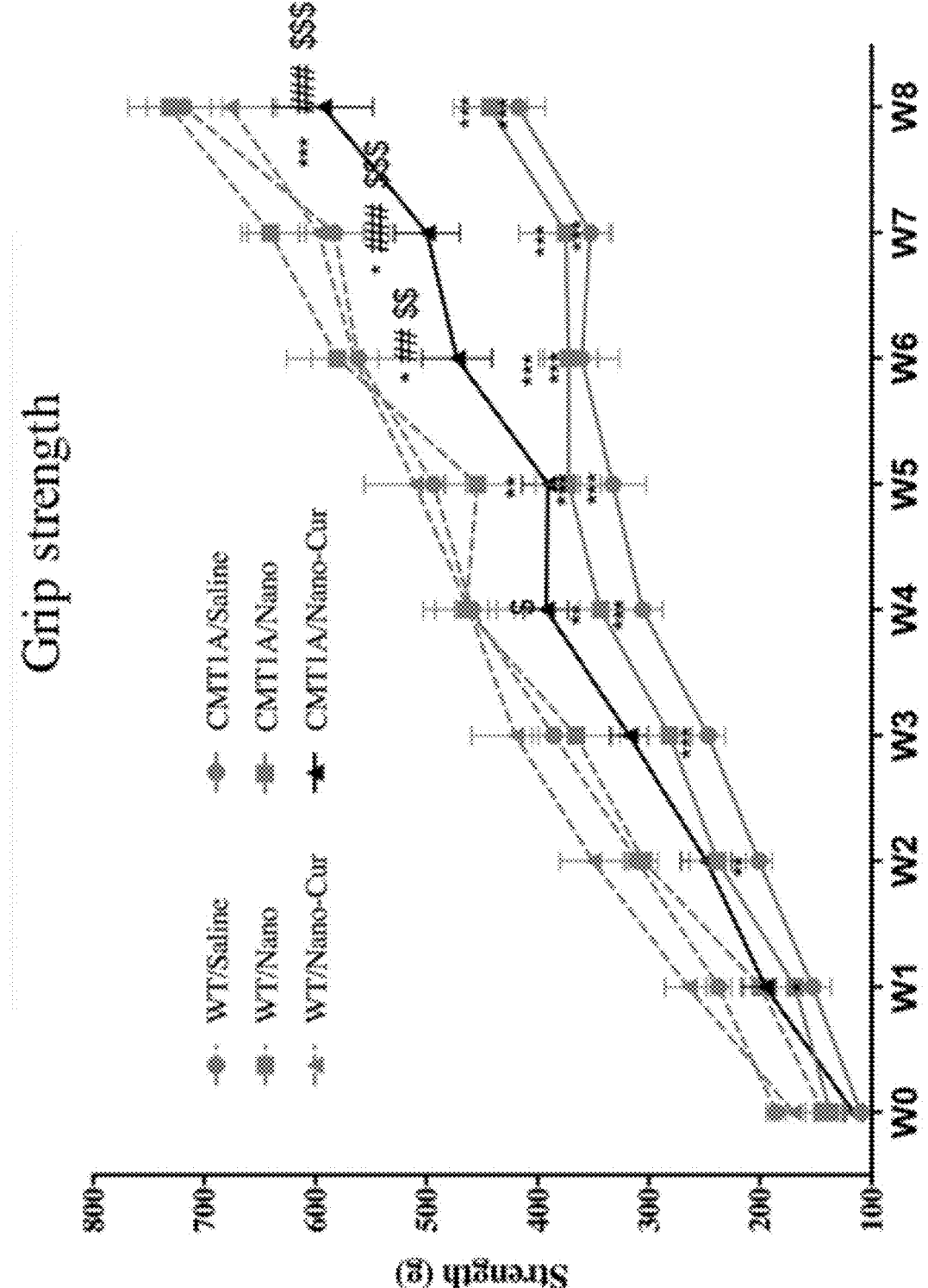
FIG. 2A: graphical representation of the gripping strength of the lower limbs of WT or CMT1A rats as a function of the duration of treatment with: either saline solution, either cellulose-$\beta$-cyclodextrin nanocrystals diluted in saline solution (Nano), either Nano-Cur (W: week). Data are expressed as the mean+/−standard error using a two-factor ANOVA and Dunnett's post-hoc test (*: $p < 0.05$, : $p < 0.01$ and *: $p < 0.001$ vs. WT/saline solution group) and a two-factor ANOVA followed by a Tukey post-hoc test (#: $p < 0.05$, ##: $p < 0.01$, and ###: $p < 0.001$ vs. CMT1A/saline solution group; $: $p < 0.05$, $$: $p < 0.01$, and $$$: $p < 0.001$ vs. CMT1A/Nano group).

FIG. 2A shows the gripping performance of the animals' hind legs measured using the gripping force test. A significant decrease in grip strength was revealed in CMT1A/saline solution rats compared to WT/saline solution rats at weeks W1 ($p<0.05$), W2, W3 ($p<0.01$), W4, W5, W6, W7 and W8 ($p<0.001$). In a similar manner, a loss of gripping strength performance was observed in CMT1A/Nano rats compared to WT/saline solution rats at weeks W4 ($p<0.01$), W5, W6, W7 and W8 ($p<0.001$). Interestingly, the analyses showed a significant improvement in gripping strength in CMT1A/Nano-Cur rats compared to CMT1A/saline solution rats at weeks W4 ($p<0.05$), W6 ($p<0.01$), W7, and W8 ($p<0.001$). Similarly, an increase in gripping strength was observed in CMT1A/Nano-Cur rats compared to CMT1A/Nano rats at weeks W6 ($p<0.001$), W7 ($p<0.001$), and W8 ($p<0.001$). These results therefore suggest that Nano-Cur treatment limits the loss of gripping strength observed in CMT1A rats.

Figure 2B:
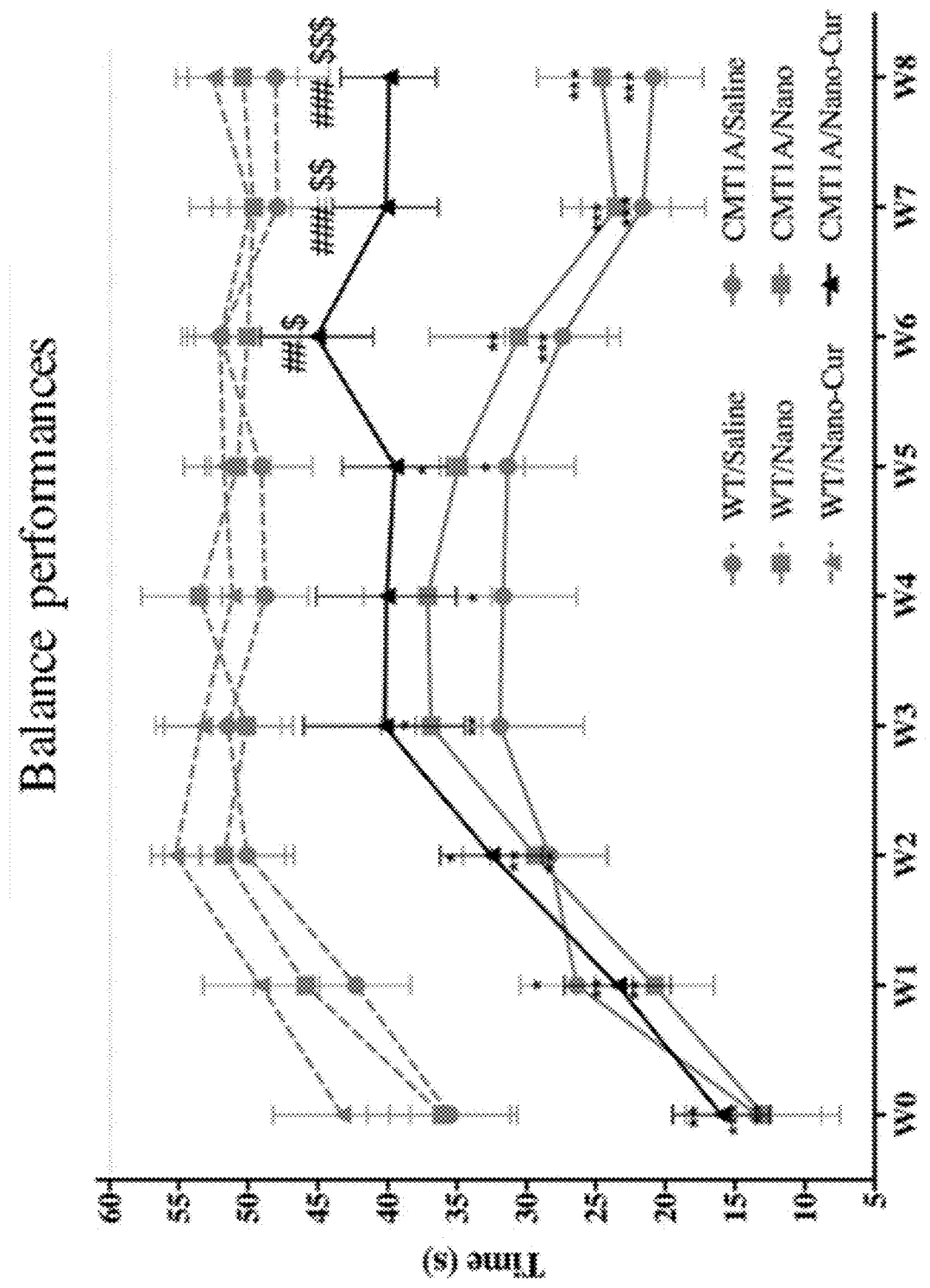
FIG. 2B: graphical representation of the steady-state balance performance (bar test) of WT or CMT1A rats as a function of the duration of treatment with: either saline solution, Nano, or Nano-Cur.

The balance of the animals was assessed using the one-bar hold test (FIG. 2B). A significant decrease in balance time was observed in CMT1A/saline solution rats compared to WT/saline solution rats at W0, W1, W2, W3 ($p<0.01$), W4, W5 ($p<0.05$), W6, W7, and W8 ($p<0.001$). Similarly, a significant decrease in balance performance was observed in CMT1A/Nano rats compared with WT/Nano rats at W0 ($p<0.001$), W1, W2 ($p<0.01$), W3, W5 ($p<0.05$), W6, W7 and W8 ($p<0.001$). Statistical analyses using data from CMT1A/Nano-Cur rats indicated a significant decrease in balance performance over the first three weeks of treatment compared to CMT1A/saline solution animals (W0: $p<0.01$, W1: $p<0.05$, and W2: $p<0.05$). However, no significant difference was observed between the CMT1A/Nano-Cur and WT/saline solution groups during the last 6 weeks of treatment. Interestingly, a significant improvement in balance performance was noted in CMT1A/Nano-Cur rats compared to CMT1A/saline solution rats (W6: $p<0.01$, W7 and W8: $p<0.001$) and CMT1A/Nano rats (W6: $p<0.05$, W7: $p<0.01$, and W8: $p<0.001$) at weeks W6, W7 and W8. These results suggest a beneficial effect of Nano-Cur treatment on the balance performance of CMT1A rats.

Figure 2C:
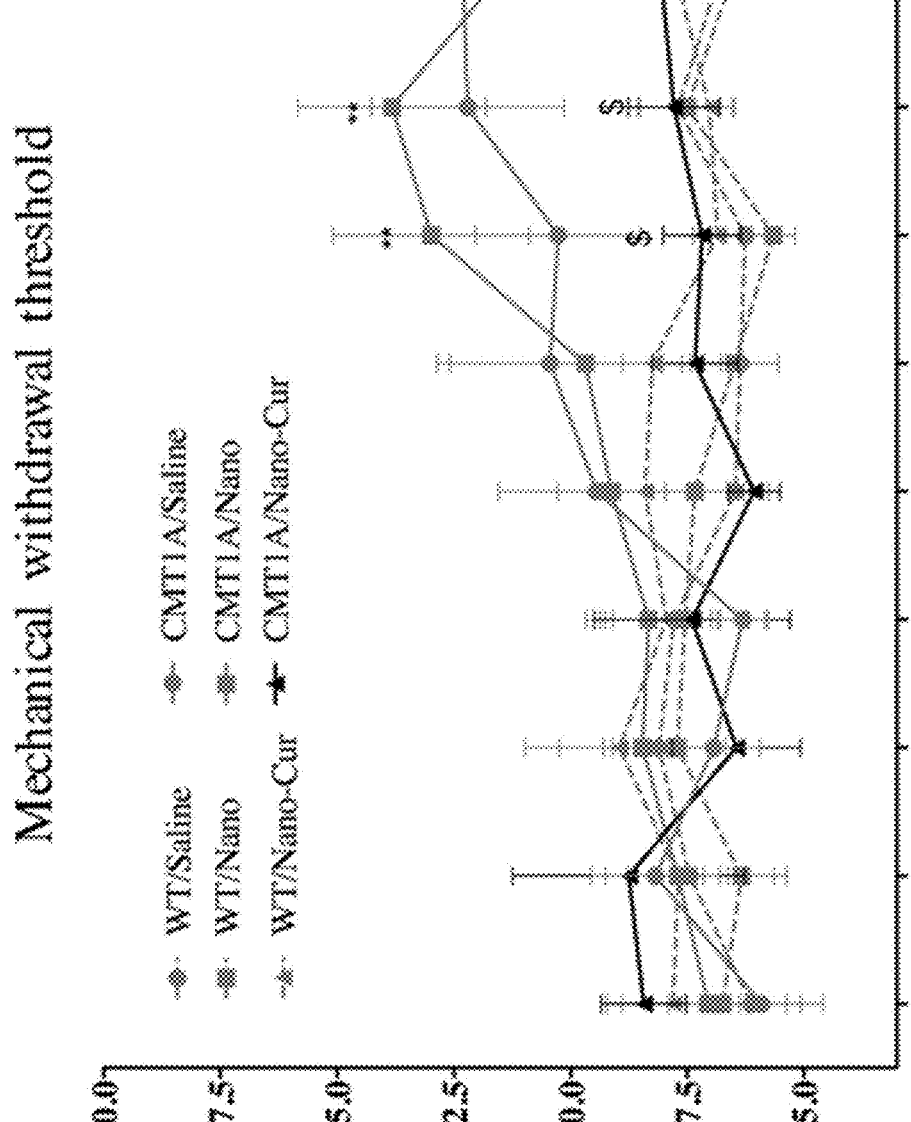
FIG. 2C: graphical representation of the withdrawal threshold to a mechanical paw stimulus (von Frey filament test) of WT or CMT1A rats as a function of the duration of treatment with: either saline solution, Nano, or Nano-Cur.

The response to a mechanical stimulus was assessed using the von Frey filament test (FIG. 2C). At week W8, a significant increase in pressure causing paw withdrawal was observed in CMT1A/saline solution animals compared to WT/saline solution animals (W8: $p<0.05$) and a trend in this direction at weeks W6 and W7. Also, at W6, W7 and W8, a significant decrease in tactile sensitivity was observed in CMT1A/Nano rats compared to WT/saline solution rats (W6: $p<0.01$; W7: $p<0.01$ and W8: $p<0.05$). Interestingly, a significant improvement in tactile sensitivity was shown in CMT1A/Nano-Cur animals at W6 ($p<0.05$) and W7 ($p<0.05$) compared with CMT1A/Nano rats. In addition, statistical analysis indicated no significant difference during the 8-week test between the CMT1A/Nano-Cur and WT/saline solution groups. These results suggest that Nano-Cur treatment limits the loss of tactile sensitivity in CMT1A rats.

Figure 2D:
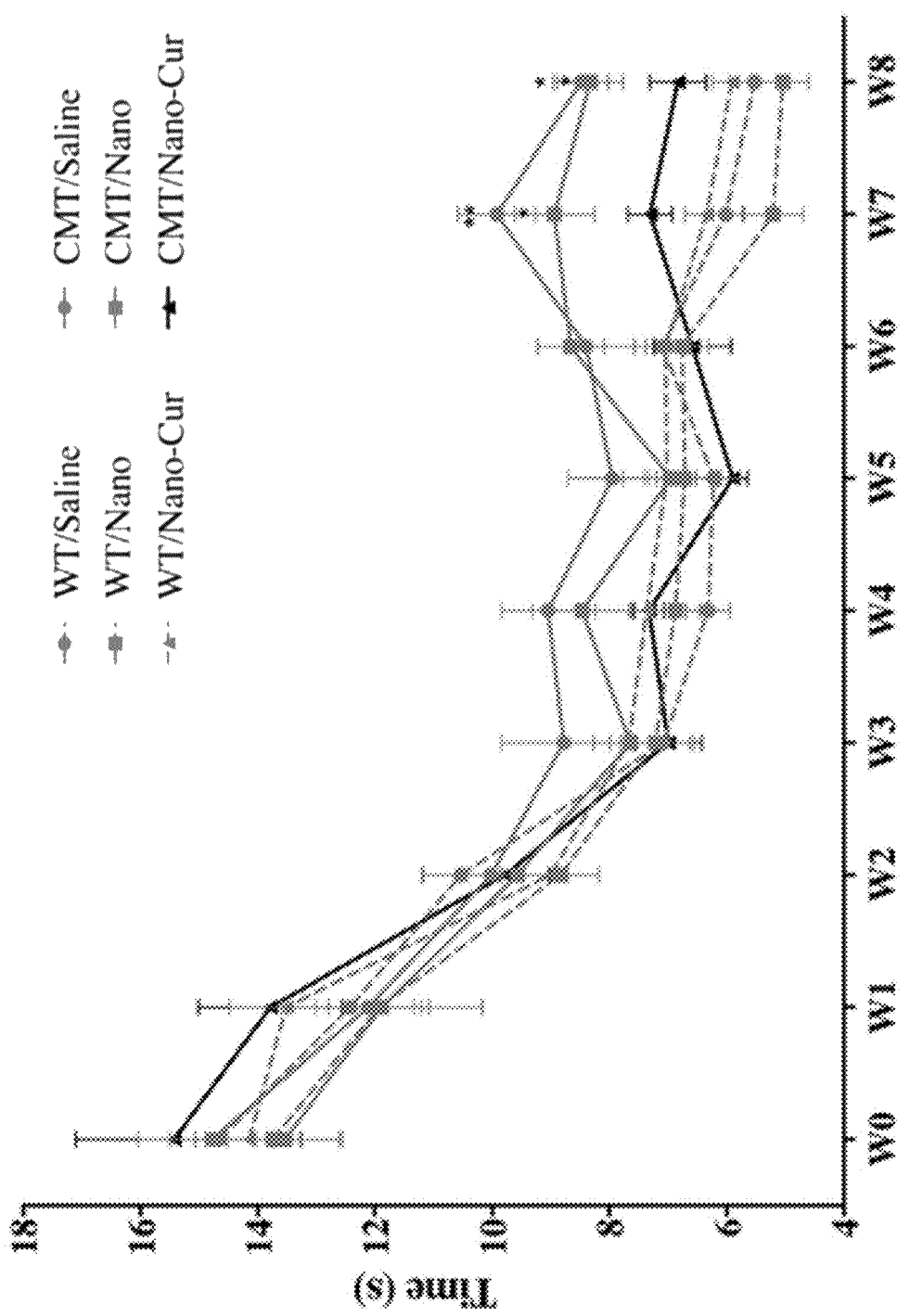
FIG. 2D: graphical representation of the withdrawal threshold to a thermal stimulus of the paw (hot plate test) of WT or CMT1A rats as a function of the duration of treatment with: either saline solution, Nano, or Nano-Cur.

The response to a thermal stimulus was assessed using the hot plate test (FIG. 2D). At weeks W7 and W8, a significant increase in paw withdrawal latency was observed in CMT1A/saline solution and CMT1A/Nano rats compared to WT/saline solution rats (CMT1A/saline solution: W7 $p<0.01$ and W8 $p<0.05$, CMT1A/Nano: W7 $p<0.05$ and W8 $p<0.05$). In contrast, no significant difference in thermal sensitivity was observed between WT/saline solution and CMT1A/Nano-Cur rats during the 8 weeks of treatment. These results suggest that Nano-Cur treatment improves the thermal sensitivity of CMT1A rats.

Electromyographic analysis was performed at week 8 (Table 2). Statistical analyses were performed using motor nerve conduction velocity (MNCV) and M-wave amplitude data: they indicated no significant difference between all WT groups. In contrast, a decrease in NMCV and M-wave amplitude was observed in all CMT1A groups. Nevertheless, an increase in NMCV and M-wave amplitude was observed in CMT1A/Nano-Cur rats compared with CMT1A/saline solution rats ($p<0.001$) or CMT1A/Nano rats ($p<0.001$). Analyses of sensitive nerve conduction velocity (SNCV) and H-reflex amplitude data did not indicate significant differences between all WT groups. In CMT1A/Nano-Cur rats, it was possible to record the H-reflex (in contrast to the other two groups of CMT1A rats), thus allowing calculation of SNCV, which nevertheless remained lower than that of WT/saline solution rats (H-reflex amplitude: $p<-0.001$, SNCV: $p<-0.001$). These results suggest that Nano-Cur treatment limits the decrease in electrophysiological parameters observed in CMT1A rats.

TABLE 2

| Electrophysiological recordings | | | | | | |
|---|---|---|---|---|---|---|
| | WT/ saline solution | WT/Nano | WT/ Nano-Cur | CMT1A/ saline solution | CMT1A/ Nano | CMT1A/ Nano-Cur |
| MNCV (m/s) | 39.9 (±4.7) | 41.5 (+5.0) | 39.5 (±3.8) | 14.1 (±1.2)*** | 14.9 (±1.3)*** | 25.0 (±2.4)** ### $$$ |
| M-wave amplitude (mV) | 15.7 (±0.9) | 14.9 (±0.9) | 14.8 (±1.2) | 2.5 (±0.5)*** | 2.3 (±0.5)*** | 7.2 (±0.7)*** ### $$$ |

TABLE 2-continued

| | WT/ saline solution | WT/Nano | WT/ Nano-Cur | CMT1A/ saline solution | CMT1A/ Nano | CMT1A/ Nano-Cur |
|---|---|---|---|---|---|---|
| SNCV (m/s) | 35.9 (±3.9) | 37.4 (±3.8) | 37.4 (±3.8) | N.D. | N.D. | 12.5 (±1.7)*** |
| H-reflex amplitude | 1.6 (±0.3) | 1.7 (±0.3) | 1.6 (±0.2) | N.D. | N.D. | 0.4 (±0.1)*** |

Electrophysiology values are expressed as mean ± standard error (SEM). The results are compared using a 1-factor ANOVA and Dunnett's post-hoc test (*p < 0.05, p < 0.01, and *p < 0.001 vs. WT/saline solution group) and using a 1-factor ANOVA followed by Tukey's post-hoc test (#: p < 0.05, ##: p < 0.01, and ###: p < 0.001 vs CMT1A/saline solution group; $: p < 0.05, $$: p < 0.01, and $$$: p < 0.001 vs. CMT1A/Nano group).

Example 3: Nano-Cur Treatment Limits Muscle Damage in CMT1A Rats

Figure 3A:
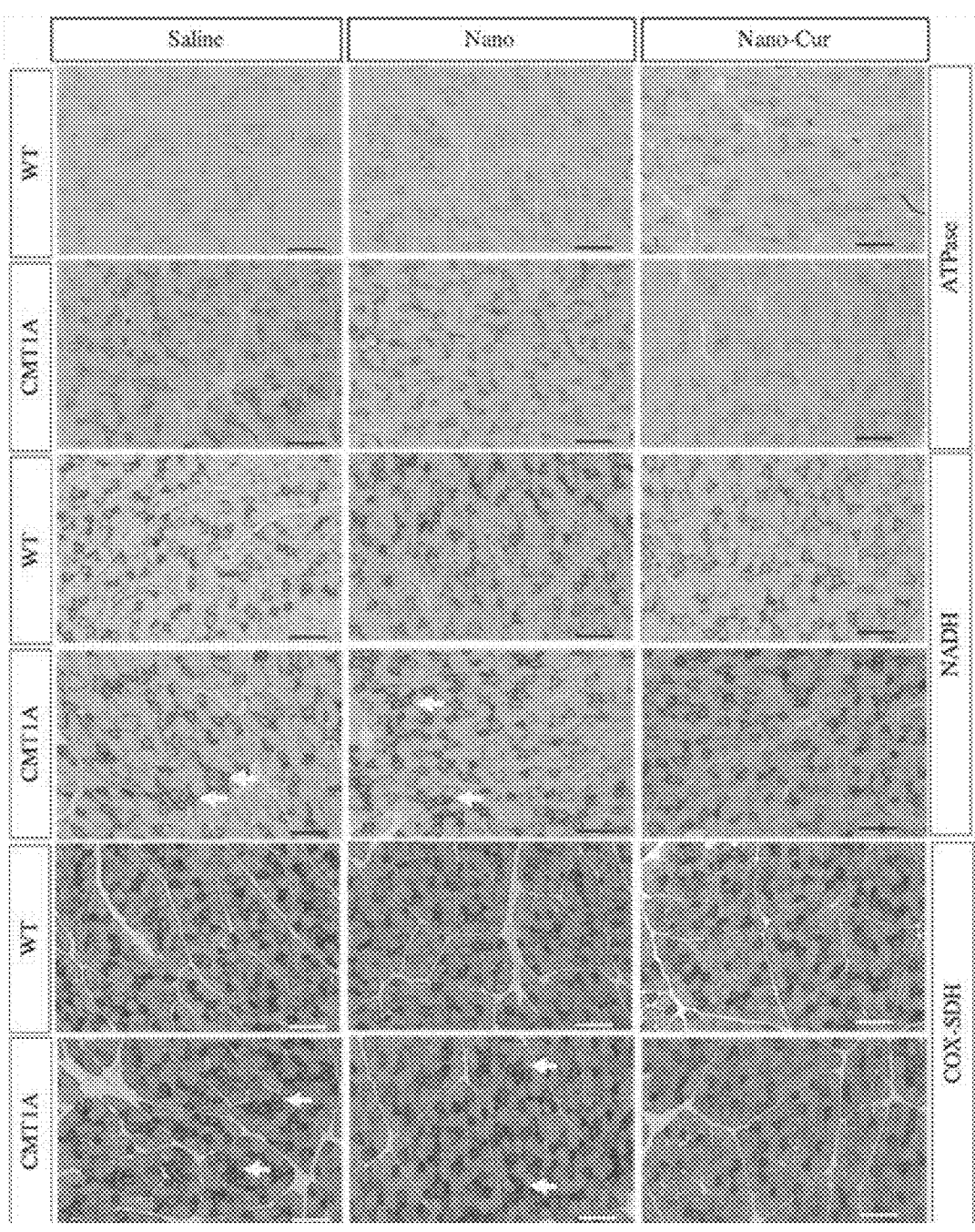
FIG. 3A: optical microscope imaging of staining of gastrocnemius muscle sections from WT or CMT1A rats revealing i) ATPase to assess skeletal muscle fiber distribution, ii) NADH (nicotinamide adenine dinucleotide) to assess muscle fiber type pattern, iii) cytochrome oxidase/succinic dehydrogenase (COX-SDH) to show the pattern of muscle fiber types, fibers with abnormal mitochondria and fibers lacking cytochrome oxidase. White arrows indicate the presence of clusters (aggregates) of muscle fibers. Scale bar: 100 μm.

ATPase staining was used to assess the distribution of skeletal muscle fibers. Combined cytochrome oxidase and succinic acid dehydrogenase (COX-SDH) staining was used to show the type of muscle fibers, fibers with abnormal mitochondria and fibers lacking cytochrome oxidase. NADH staining was used to assess muscle fiber type, mitochondria distribution, and myofibril disruption. Microscopic analysis of these different histochemical stains showed no difference in gastrocnemius muscle fiber size or mitochondria distribution in all groups of rats at W8. Clustering of type I and/or type II muscle fibers is an early sign of muscle damage. Referring to FIG. 3A, a trend of muscle fiber clustering was observed in CMT1A/saline and CMT1A/Nano rats compared with WT/saline solution rats. However, this clustering of muscle fibers was not observed in CMT1A/Nano-Cur rats.

Figure 3B:
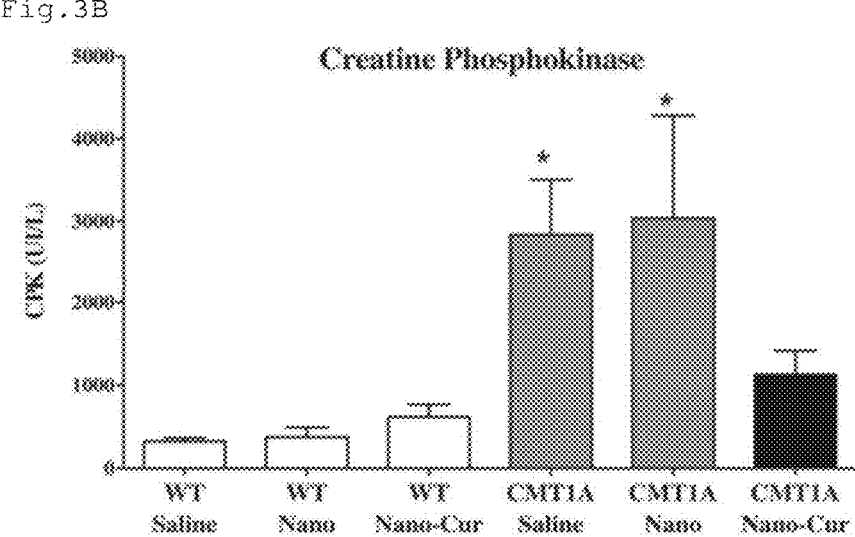
FIG. 3B: graphical representation of creatine phosphokinase (CPK) dosage as a marker of muscle lysis.

In addition, plasma assays of muscle lysis markers (creatine phosphokinase CPK and creatinine) showed an increase in CPK (p<0.05) (FIG. 3B) and a decrease in creatinine (p<0.05) (FIG. 3C) in CMT1A/saline solution rats compared with the WT/saline solution group. No significant differences were observed in CPK and creatinine levels in CMT1A/Nano-Cur rats compared with WT/saline solution rats. These results indicate a beneficial effect of Nano-Cur treatment on the integrity of gastrocnemius muscle tissue in CMT1A rats.

Example 4: Nano-Cur Treatment Limits Demyelination In Vivo and Improves Myelination In Vitro Morphometric analyses were performed using microscopic images obtained from semi-fine sections (W8). No significant differences in morphometric parameters were identified between all WT groups. In addition, no significant difference was observed in the number of myelinated axons between all groups (Table 3). Compared with WT/saline solution rats, mean axon diameter and mean fiber diameter (axon+myelin) were significantly reduced in all CMT1A groups (p<0.001). However, a significant increase in myelinated fiber diameter was observed in the CMT1A/NanoCur group compared with the CMT1A/Nano group (p<0.05). A significant decrease in myelin thickness was observed in all CMT1A groups (p<0.001) compared with the WT/saline solution group. In contrast, a significant increase in myelin thickness in CMT1A/Nano-Cur rats was demonstrated compared with CMT1A/saline solution rats (p<0.05) or CMT1A/Nano rats (p<0.05).

Similarly, a decrease in G-ratio was observed in all CMT1A groups (p<0.001) compared with the WT/saline solution group. Nevertheless, a significant increase in G-ratio was observed in CMT1A/Nano-Cur rats compared to CMT1A/saline solution group (p<0.05) and also a significant increase in myelin thickness compared to CMT1A/saline solution (p<0.05) or CMT1A/Nano (p<0.05) animals.

TABLE 3

Characteristics of myelinated axons: total number, mean axon diameter and mean fiber diameter (axon + myelin), G-ratio and myelin thickness

| | WT/ saline solution | WT/Nano | WT/ Nano-Cur | CMT1A/ saline solution | CMT1A/ Nano | CMT1A/ Nano-Cur |
|---|---|---|---|---|---|---|
| Number of axons | 1796 (±62.1) | 1766 (±71.5) | 1741 (±58.1) | 1636 (±44.2) | 1616 (±58.6) | 1679 (±64.1) |
| Axon diameter | 5.7 (±0.2) | 5.6 (±0.2) | 5.6 (±0.2) | 4.3 (±0.1)*** | 4.1 (±0.2)*** | 4.4 (±0.1)*** |
| Fiber diameter | 9.8 (±0.3) | 9.6 (±0.2) | 9.9 (±0.3) | 5.9 (±0.2)*** | 5.8 (±0.2)*** | 6.7 (±0.3)***$ |
| G-ratio | 0.57 (±0.01) | 0.57 (±0.01) | 0.56 (±0.01) | 0.71 (±0.01)*** | 0.69 (±0.02)*** | 0.64 (±0.01)** # |
| Myelin thickness | 2.05 (±0.08) | 2.00 (±0.04) | 2.12 (±0.07) | 0.88 (±0.02)*** | 0.86 (±0.03)*** | 1.18 (±0.10)*** #$ |

Results are compared using a one-factor ANOVA and Dunnett's post-hoc test (*p < 0.05, p < 0.01, and *p < 0.001 vs. WT/saline solution group) and using a one-factor ANOVA followed by Tukey's post-hoc test (#: p < 0.05, ##: p < 0.01, and ###: p < 0.001 vs. CMT1A/saline solution group; $: p < 0.05, $$: p < 0.01, and $$$: p < 0.001 vs CMT1A/Nano group).

Figure 4A:
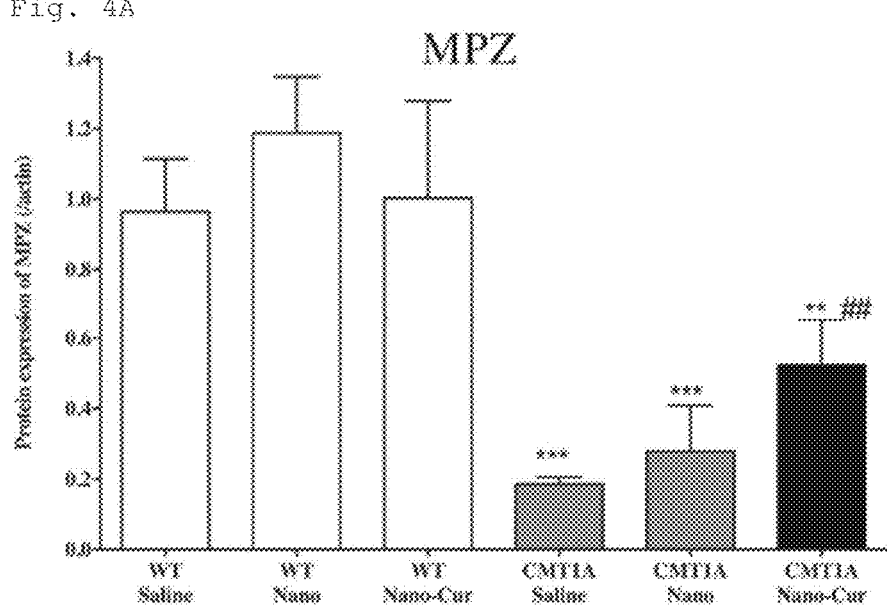
FIG. 4A: graphical representation of the MPZ (myelin protein zero) immunoblot result indicating the protein expression level in the different groups of rats tested. The data are compared using a one-factor ANOVA and Dunnett's post-hoc test (*: $p < 0.05$, : $p < 0.01$ and *: $p < 0.001$ vs. WT/saline solution group) and a one-factor ANOVA followed by Tukey's post-hoc test (#: $p < 0.05$, ##: $p < 0.01$, and ###: $p < 0.001$ compared with CMT1A/saline solution group; $: $p < 0.05$, $$: $p < 0.01$, and $$$: $p < 0.001$ compared with CMT1A/Nano group).
Figure 4B:
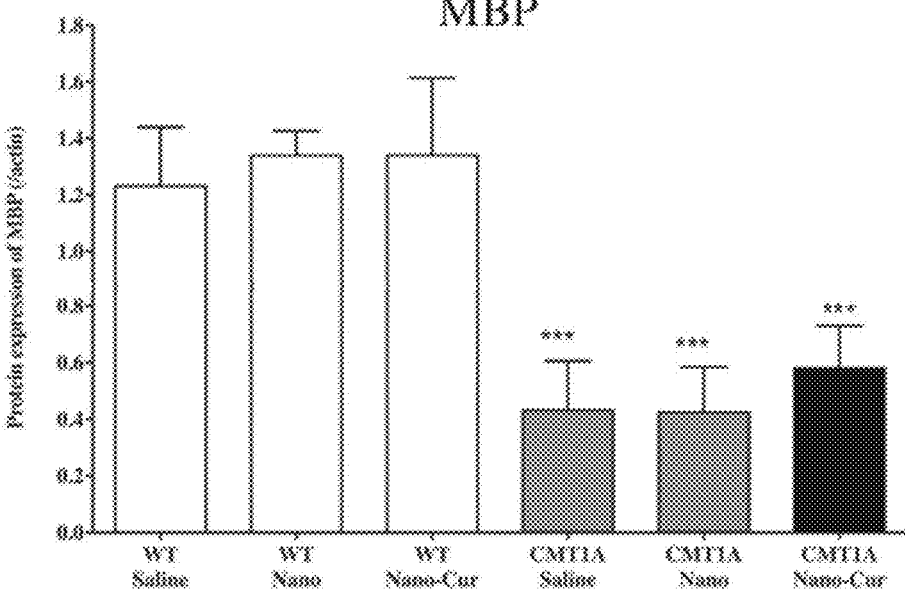
FIG. 4B: graphical representation of the MBP (myelin basic protein) immunoblot result showing the expression level of the protein in the different groups of rats tested.
Figure 4C:
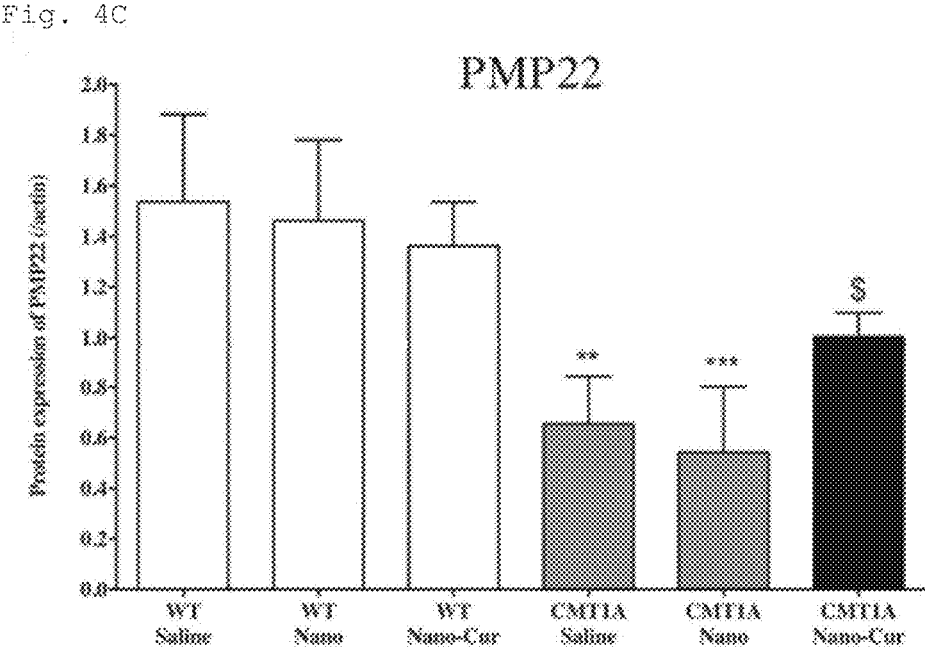
FIG. 4C: graphical representation of the PMP22 (peripheral myelin protein 22) immunoblot result showing the expression level of the protein in the different groups of rats tested.
Figure 4D:
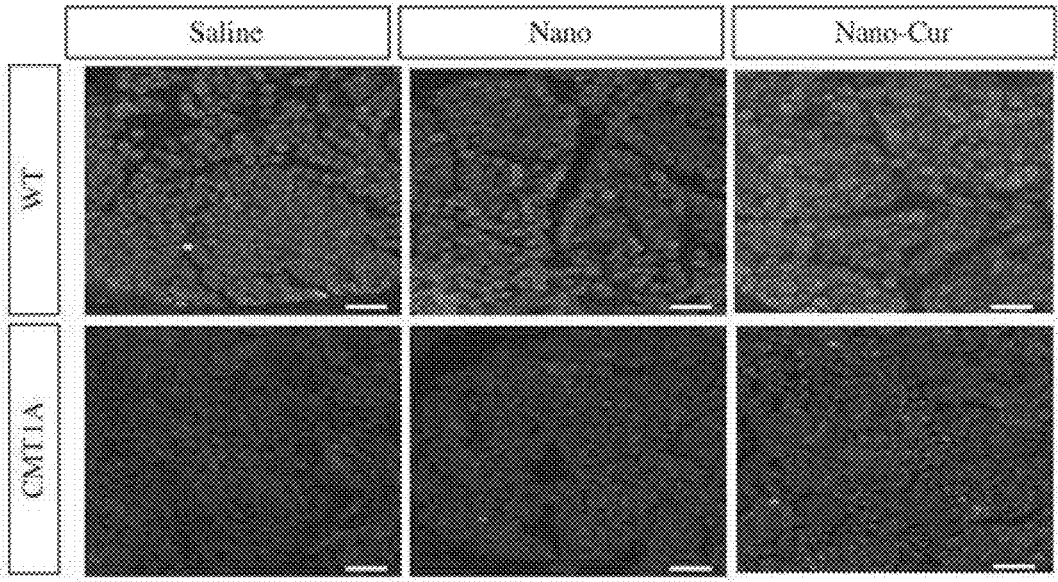
FIG. 4D: anti-PMP22 immunohistochemistry on sciatic nerve sections from WT rats or CMT1A rats. Scale bar: 100 μm.

Expression of Myelin Protein Zero (MPZ), Myelin Basic Protein (MBP), and Peripheral Myelin Protein 22 (PMP22) was assessed in sciatic nerve homogenates at W8 (FIGS. 4A-C). No significant differences were observed in the expression of these proteins between all WT groups. Compared with WT/saline solution rats, a significant decrease in MPZ expression was observed in all CMT1A groups (p<0.001)(FIG. 4A). Also, an increased MPZ expression was observed in CMT1A/Nano-Cur rats (p-<–0.05) compared with CMT1A/saline solution rats (FIG. 4A). Similarly, a decrease in MBP expression was also observed in all CMT1A groups (p<0.001) compared with WT/saline solution rats (FIG. 4B). In addition, a decrease in PMP22 expression was observed in CMT1A/saline solution rats (p<0.001) and CMT1A/Nano rats (p<0.001) compared with WT rats. However, no difference in PMP22 expression levels was observed between WT/saline solution animals and CMT1A/Nano-Cur animals (FIG. 4C). Finally, increased PMP22 expression was also observed in CMT1A/Nano-Cur rats (p-<–0.05) compared with CMT1A/Nano rats. These results were confirmed by immunofluorescent labeling of PMP22 on sciatic nerve sections at W8 (FIG. 4D).

Figure 4E:
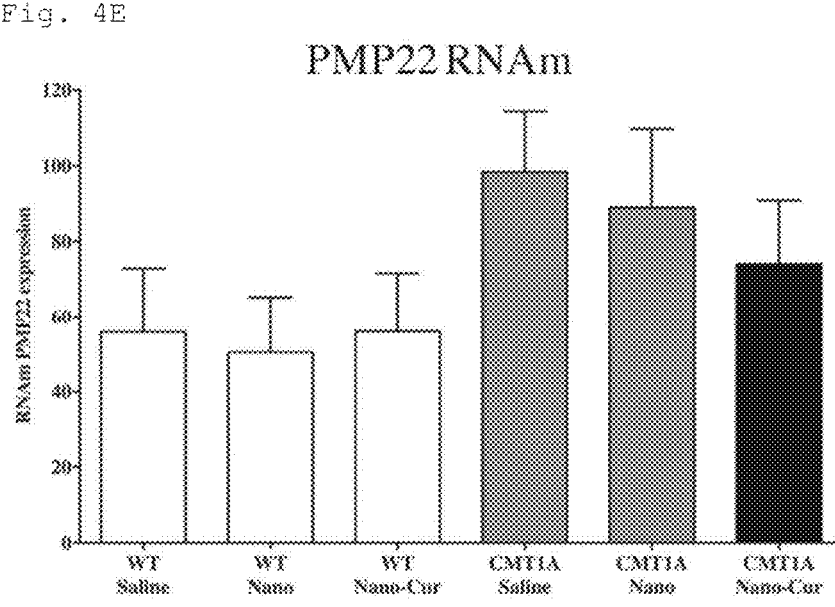
FIG. 4E: graphical representation of PMP22 mRNA quantification in WT wild type rats or CMT1A rats.

Thus, PMP22 mRNA expression was assessed in sciatic nerve homogenates at W8 (FIG. 4E). No significant difference was observed in PMP22 mRNA expression between all WT groups. However, a significant increase in PMP22 mRNA expression was identified in CMT1A/saline solution rats (p<0.01) compared with WT/saline solution animals.

Similarly, an increase in PMP22 mRNA expression was observed in CMT1A/Nano rats compared with WT/Nano rats. In contrast, no significant difference was observed between the WT/saline solution and CMT1A/Nano-Cur groups. These results suggest that Nano-Cur treatment promotes myelination in CMT1A rats.

Figure 5A:
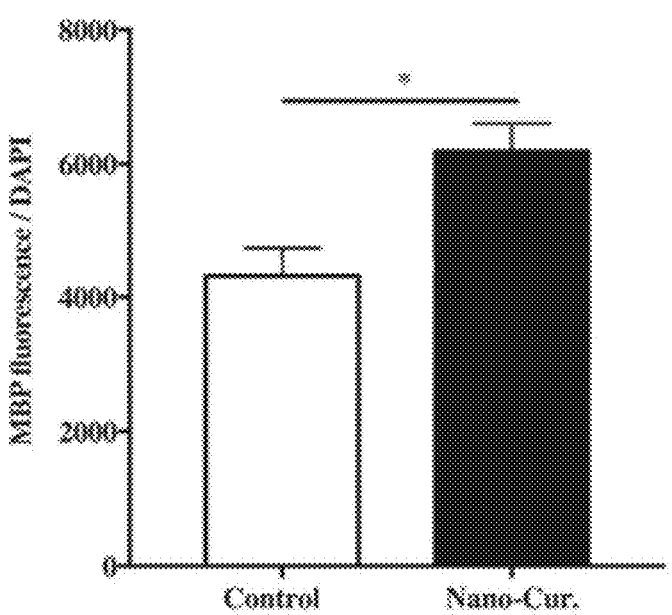
FIG. 5A: graphical representation of MBP (myelin basic protein) fluorescence intensity in a co-culture of Schwann cells and WT neurons (control) treated or not by Nano-Cur. The results are compared using a t-test (*: $p<0.05$, : $p<0.01$ and *: $p<0.001$ vs. control).
Figure 5B:
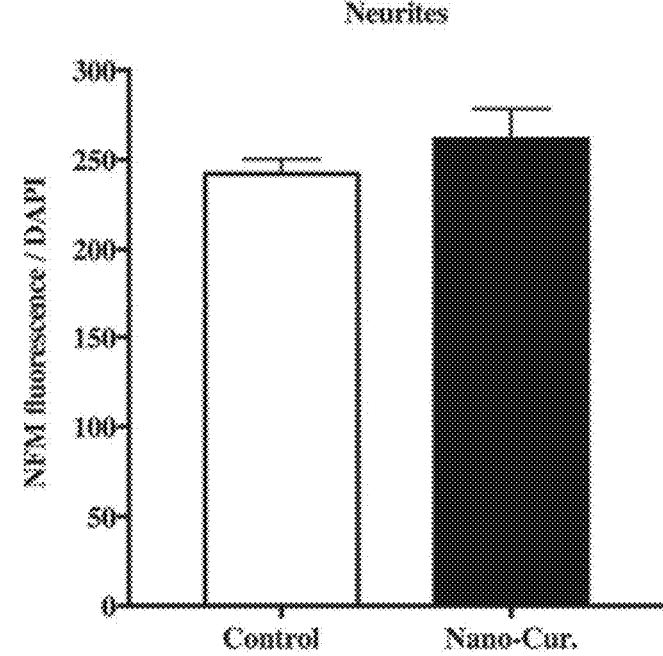
FIG. 5B: graphical representation of the fluorescence intensity of NFM (neurofilament) in a co-culture of Schwann cells and WT neurons (control) treated or not by Nano-Cur, allowing to evaluate the amount of neurites.
Figure 5C:
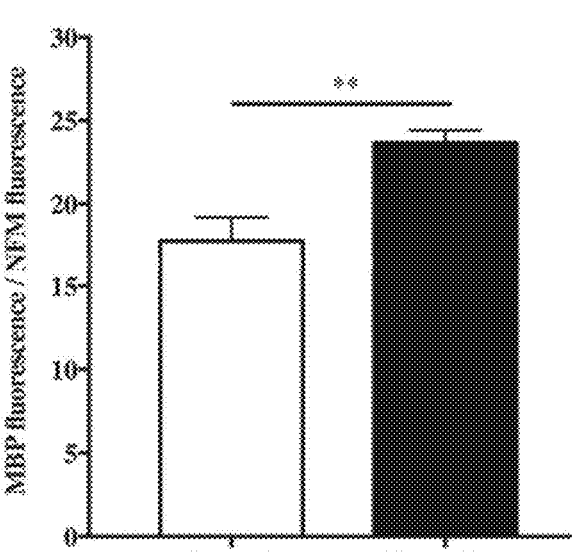
FIG. 5C: graphical representation of the MBP/NFM ratio in a co-culture of Schwann cells and WT neurons treated or not by Nano-Cur, allowing to evaluate the myelination.

Myelination was assessed in vitro by immunofluorescent labeling of MBP (myelin labeling) and NFM (neurite labeling) from co-cultures of Schwann cells and neurons from WT rats (data not shown). These results indicate that Nano-Cur treatment induces a significant increase in MBP expression in vitro compared to the control condition without treatment (p<0.05) (FIG. 5A). However, there was no significant effect of Nano-Cur treatment on NFM expression compared to the control condition (FIG. 5B). Furthermore, analysis of MBP/NFM ratio data indicated a significant increase in myelination with Nano-Cur treatment (p<0.01) (FIG. 5C). These results suggest that Nano-Cur treatment enhances myelination in vitro from co-cultures of Schwann cells and neurons.

Figure 6A:
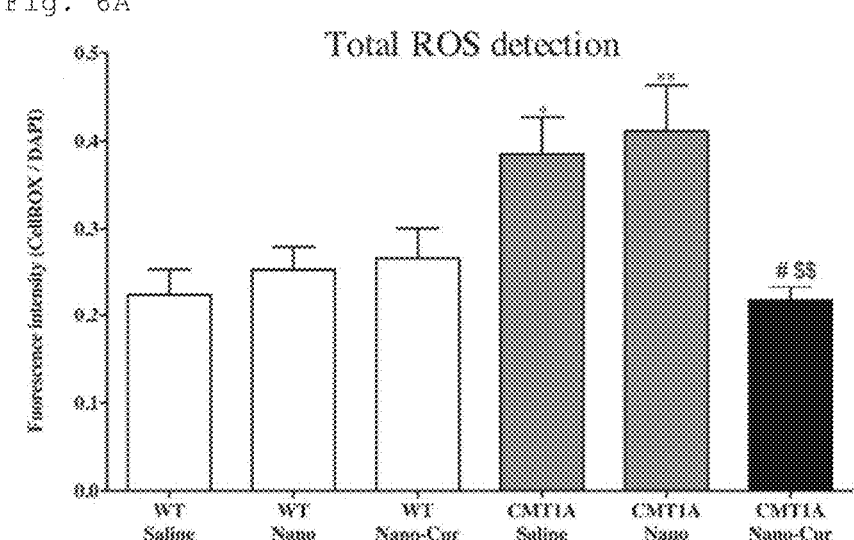
FIG. 6A: graphical representation of fluorescence intensity as a measure of total reactive oxygen species (ROS) using the cellROX method in sciatic nerves of WT wild type rats or CMT1A rats treated or not with Nano-Cur. The results are compared using a one-factor ANOVA and Dunnett's post-hoc test (*: $p<0.05$, : $p<0.01$, and *: $p<0.001$ vs. WT/saline solution group) and a one-factor ANOVA followed by Tukey's post-hoc test (#: $p<0.05$, ##: $p<0.01$, and ###: $p<0.001$ vs. CMT1A/saline solution group; $: $p<0.05$, $$: $p<0.01$, and $$$: $p<0.001$ vs. CMT1A/Nano group).

Example 5: Nano-Cur Treatment Decreases Oxidative Stress and Induces Antioxidant Enzyme Expression in CMT1A Rats Oxidative stress was assessed by quantification of reactive oxygen species (ROS) from sciatic nerve sections at W8 (FIG. 6A). Referring to FIG. 6A, a significant increase in total ROS was observed in CMT1A/saline solution rats (p<0.05) and CMT1A/Nano rats (p<0.01) compared with WT/saline solution rats. Interestingly, in the sciatic nerves of CMT1A rats treated with Nano-Cur, no significant difference was observed compared to the WT/saline solution group. Furthermore, a significant decrease in ROS content was observed in CMT1A/Nano-Cur compared to CMT1A/saline solution rats (p<0.05) and CMT1A/Nano rats (p<0.01). These results indicate a beneficial effect of Nano-Cur treatment on oxidative stress in sciatic nerves of CMT1A rats.

Figure 6B:
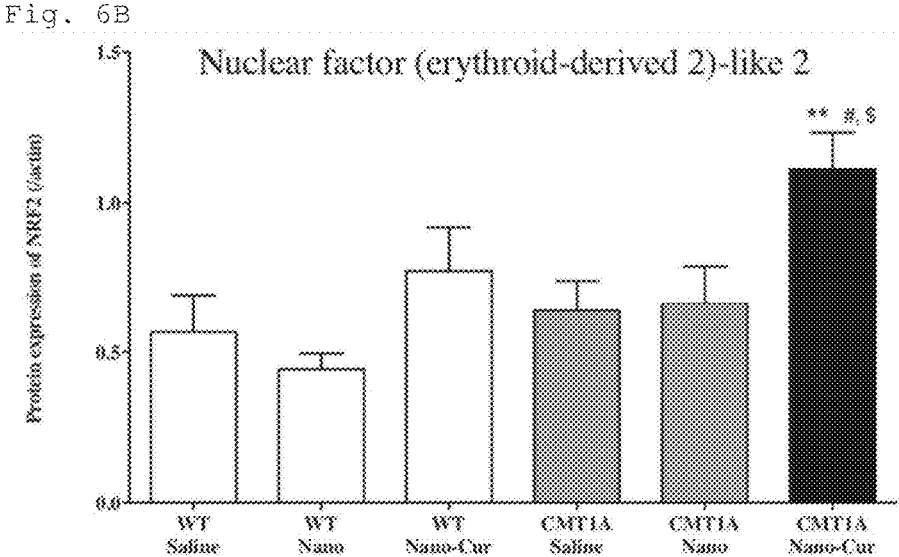
FIG. 6B: graphical representation of the expression level of nuclear factor Nrf2 (involved in the production of anti-oxidant enzymes) in WT wild type rats or CMT1A rats treated or not with Nano-Cur.

The expression of Nrf2 protein, a transcription factor involved in the production of antioxidant enzymes, was also assessed from rat sciatic nerves (FIG. 6B). Referring to FIG. 6B, no significant difference in Nrf2 expression was observed between the CMT1A/saline solution and CMT1A/Nano groups compared with the WT/saline solution group. The results showed increased expression of Nrf2 in CMT1A/Nano-Cur rats compared with WT/saline solution (p<0.01), CMT1A/saline solution (p<0.05) and CMT1A/Nano (p<0.05) rats, suggesting an antioxidant effect of Nano-Cur.

Figure 6C:
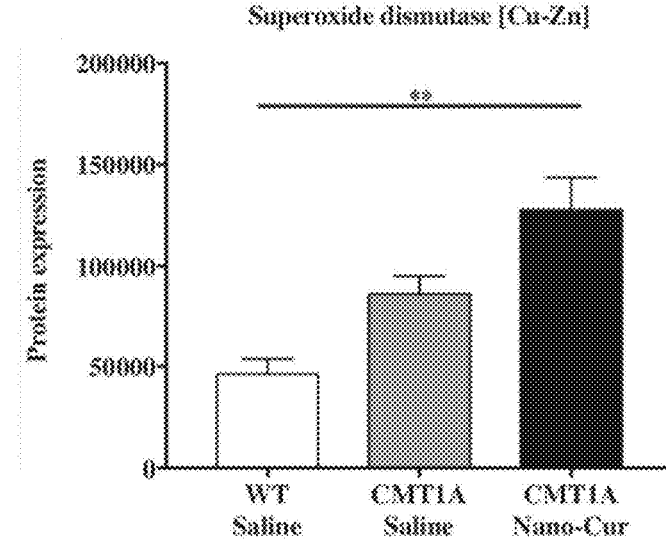
FIG. 6C: graphical representation of the expression level of superoxide dismutase [Cu—Zn] in WT wild type rats or CMT1A rats treated or not with Nano-Cur. The results are compared using a one-factor ANOVA and Tukey's post-hoc test (*: $p<0.05$, : $p<0.01$ and *: $p<0.001$ vs. WT/saline solution group).
Figure 6D:
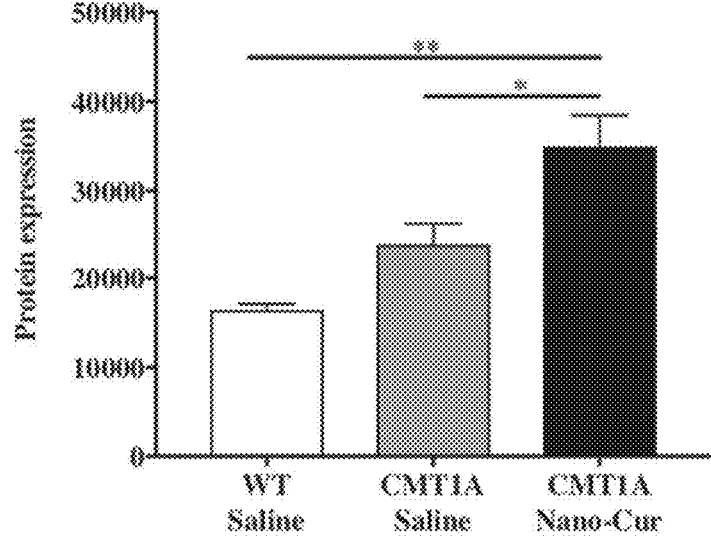
FIG. 6D: graphical representation of glutathione S-transferase alpha-3 expression level in WT wild type rats or CMT1A rats treated or not with Nano-Cur.

The expression of some antioxidant enzymes (superoxide dismutase [Cu—Zn] and glutathione S-transferase alpha-3) was also assessed by proteomic analysis (mass spectrometry) of sciatic nerve homogenates at W8 (FIGS. 6C-6D). The analyses indicated a significant increase in the expression of key antioxidant enzymes compared to WT/Saline rats (superoxide dismutase [Cu—Zn]: p<0.01; glutathione S-transferase). In addition, a significant increase in the expression of the antioxidant enzyme glutathione S-transferase alpha-3 was observed in CMT1A/Nano-Cur animals compared to CMT1A/Saline rats (p<0.05)(FIG. 6D). These results suggest that Nano-Cur treatment increases the expression of antioxidant enzymes in the sciatic nerves of CMT1A rats.

Figure 7A:
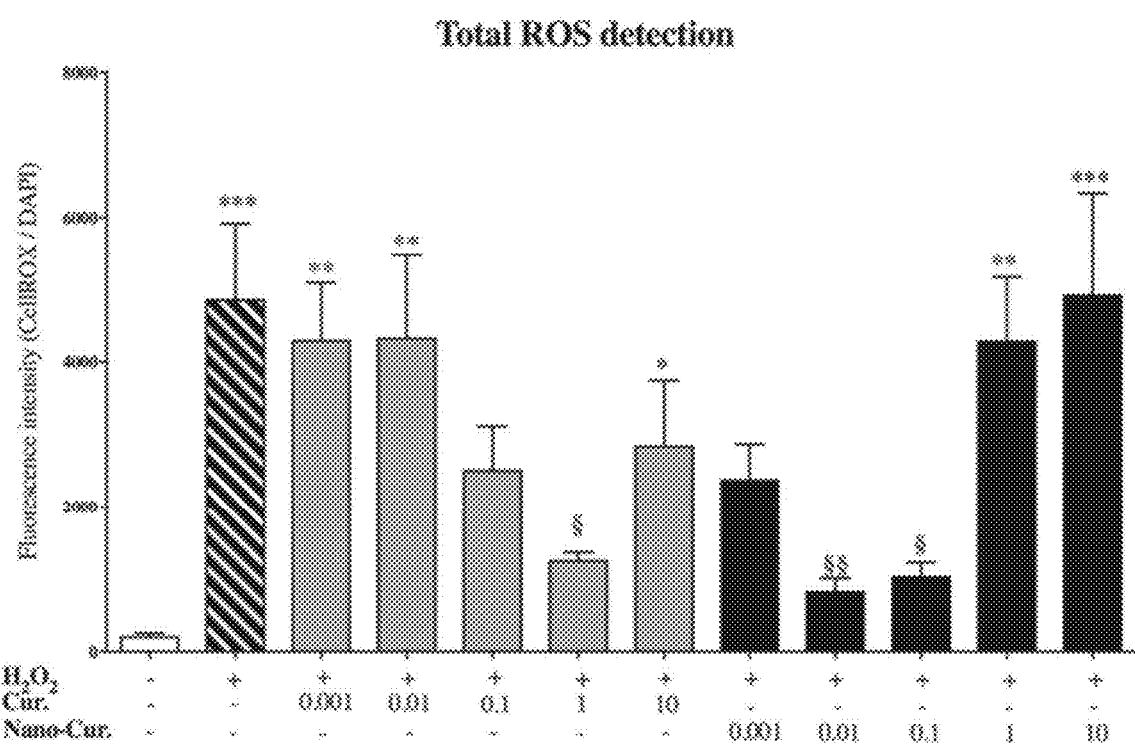
FIG. 7A: graphical representation of fluorescence intensity as a measure of total reactive oxygen species (ROS) using the cellROX method on wild type Schwann cells subjected to $H_2O_2$-induced oxidative stress as a function of various doses of curcumin alone or of Nano-Cur. The results are compared using a one-factor ANOVA and Tukey's post-hoc test (*: $p<0.05$, : $p<0.01$, and *: $p<0.001$ vs. control group; §: $p<0.05$, §§: $p<0.01$, and § § § : $p<0.001$ vs. control+curcumin group).
Figure 7B:
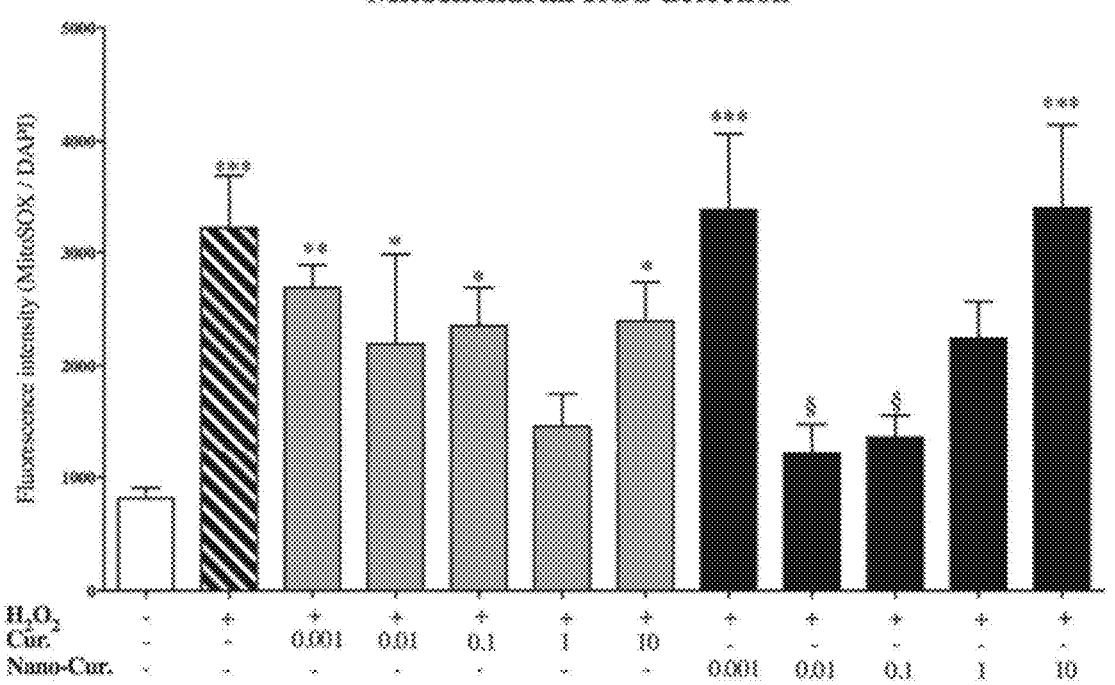
FIG. 7B: graphical representation of fluorescence intensity as a measure of superoxide production by mitochondria using the MitoSOX method on wild type Schwann cells subjected to $H_2O_2$-induced oxidative stress as a function of various doses of curcumin alone or of Nano-Cur.
Figure 7C:
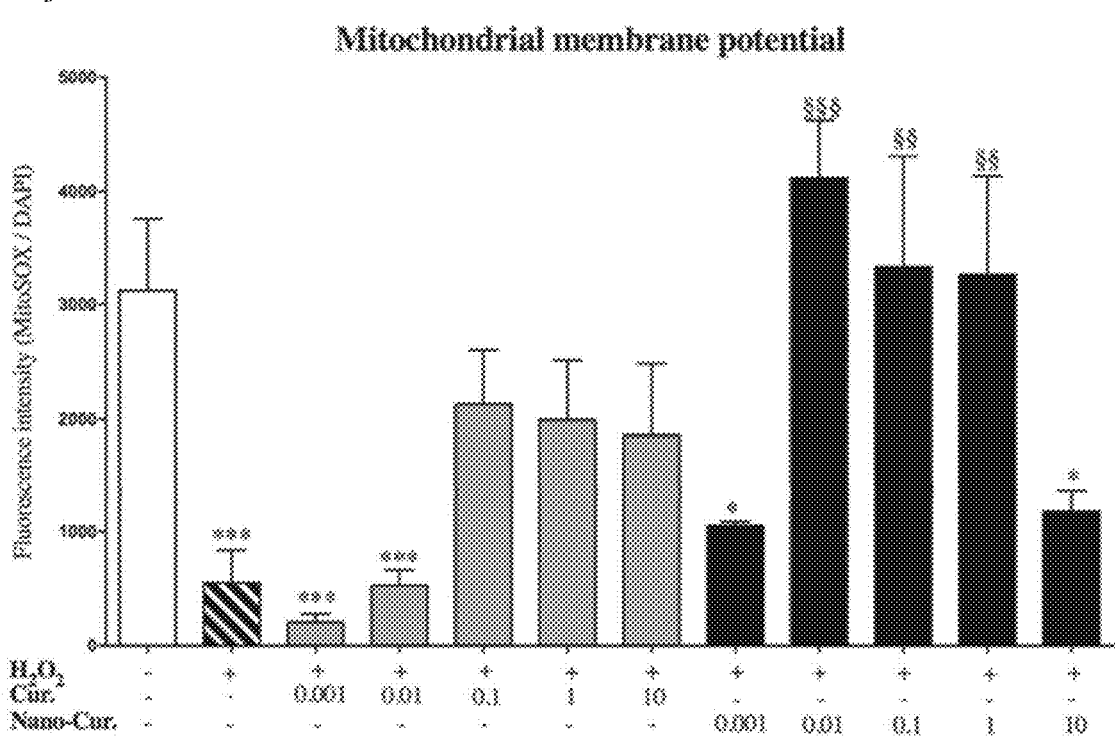
FIG. 7C: graphical representation of fluorescence intensity as a measure of mitochondrial membrane potential using the Rho123 method.

Next, the effects of curcumin alone and Nano-Cur on $H_2O_2$-induced oxidative stress were studied in vitro using primary cultures of WT rat Schwann cells. To investigate and identify the most effective dose, doses of 0.001, 0.01, 0.1, 1 and 10 µM of curcumin alone or of Nano-Cur were tested. These results indicate that $H_2O_2$ treatment (0.1 mM) induced a significant increase in total and mitochondrial ROS levels and a decrease in Δψm (index of mitochondrial membrane integrity) compared to control groups (not subjected to $H_2O_2$ treatment) (p<0.001) (FIGS. 7A-C). Referring to FIG. 7A, treatment with 1 µM curcumin alone reduced $H_2O_2$-induced total ROS (p<0.05), whereas doses of 0.001, 0.01 and 10 µM had no antioxidant effect. For Nano-Cur treatment, doses of 0.01 µM (p<0.01) and 0.1 µM (p<0.05) showed the greatest antioxidant effect.

Regarding mitochondrial ROS production, the 1 µM dose of curcumin alone restored values close to those of the control group (not subjected to $H_2O_2$ treatment) (FIG. 7B). However, Nano-Cur treatment significantly reduced $H_2O_2$-induced mitochondrial ROS at the much lower concentrations of 0.01 µM (p<0.05) and 0.1 µM (p<0.05). Similarly, referring to FIG. 7C, at concentrations of 0.001 µM and 0.01 µM curcumin alone did not reduce the $H_2O_2$-induced decrease in Δψm. In contrast, Nano-Cur doses of 0.01 µM (p<0.001), 0.1 µM (p<0.01), and 1 µM (p<0.01) significantly increased Δψm compared to the $H_2O_2$ group. These results suggest that low doses of Nano-Cur (0.01 and 0.1 µM) have the most powerful antioxidant effect.

Taken together, all these results contribute to show that Nano-Cur treatment leads to an improvement of the lesion that develops in transgenic CMT1A model rats. Indeed, the Nano-Cur treatment improves balance and grip strength and limits the loss of tactile and thermal sensitivity in CMT1A rats. The Nano-Cur treatment used in the study increased MNCV but not the amplitude of muscle action potentials. In addition, Nano-Cur treatment detected H-reflexes and thus computation of CNSV in CMT1A rats, although this signal remained weak. It is commonly accepted that MNCV is related to the integrity and thickness of the myelin sheath.

Nano-Cur treatment limited nerve demyelination/dysmyelination in CMT1A animals, with these results supported by higher expression of compact myelin proteins in treated animals. Increased oxidative stress has been described in CMT1A patients (Chahbouni et al., 2017). However, until now, oxidative stress had not been studied in the CMT1A rat model. It is known that excessive increase in ROS is deleterious to cells, especially via DNA, protein and lipid damage. Furthermore, due to the multilamellar structure of myelin, Schwann cells are particularly sensitive to lipoperoxidation. Thus, it seems appropriate to seek to reduce oxidative stress in Charcot-Marie-Tooth disease type 1A. The presented results contribute to demonstrate that a low and continuous dose of curcumin, delivered by cellulose nanocrystals, represents a promising therapy for peripheral neuropathies, including Charcot-Marie-Tooth disease type 1A, in the non-limiting form of hydrogels, subcutaneous implants, implantable pump or implanted biofunctionalized nerve conduit.

BIBLIOGRAPHIC REFERENCES

Agthong, S., Kaewsema, A., Charoensub, T., 2015. Curcumin Ameliorates Functional and Structural Abnormalities in Cisplatin-induced Neuropathy. Exp. Neurobiol. 24, 139-145.

Al Moundhri, M. S., Al-Salam, S., Al Mahrouqee, A., Beegam, S., Ali, B. H., 2013. The effect of curcumin on oxaliplatin and cisplatin neurotoxicity in rats: some behavioral, biochemical, and histopathological studies. J. Med. Toxicol. Off. J. Am. Coll. Med. Toxicol. 9, 25-33.

Caillaud M, Chantemargue B, Richard L, Vignaud L, Favreau F, Faye P-A, et al. Local low dose curcumin treatment improves functional recovery and remyelination in a rat model of sciatic nerve crush through inhibition of oxidative stress. Neuropharmacology 2018; 139: 98-116.

Chahbouni M, López M D S, Molina-Carballo A, de Haro T, Muñoz-Hoyos A, Fernández-Ortiz M, et al. Melatonin Treatment Reduces Oxidative Damage and Normalizes Plasma Pro-Inflammatory Cytokines in Patients Suffering from Charcot-Marie-Tooth Neuropathy: A Pilot Study in Three Children. Mol. Basel Switz. 2017; 22(10), 1728.

Daugherty, D. J., Marquez, A., Calcutt, N. A., Schubert, D., 2018. A novel curcumin derivative for the treatment of diabetic neuropathy. Neuropharmacology 129, 26-35.

Han, F., Luo, B., Shi, R., Han, C., Zhang, Z., Xiong, J., Jiang, M., Zhang, Z., 2014. Curcumin ameliorates rat experimental autoimmune neuritis. J. Neurosci. Res. 92, 743-750.

Kandhare, A. D., Raygude, K. S., Ghosh, P., Ghule, A. E., Bodhankar, S. L., 2012. Therapeutic role of curcumin in prevention of biochemical and behavioral aberration induced by alcoholic neuropathy in laboratory animals. Neurosci. Lett. 511, 18-22.

Kaur, M., Singh, A., Kumar, B., Singh, S. K., Bhatia, A., Gulati, M., Prakash, T., Bawa, P., Malik, A. H., 2017. Protective effect of co-administration of curcumin and sildenafil in alcohol induced neuropathy in rats. Eur. J. Pharmacol. 805, 58-66.

Khajavi M, Inoue K, Wiszniewski W, Ohyama T, Snipes G J, Lupski J R. Curcumin treatment abrogates endoplasmic reticulum retention and aggregation-induced apoptosis associated with neuropathy-causing myelin protein zero-truncating mutants. Am. J. Hum. Genet. 2005; 77: 841-850.

Khajavi M, Shiga K, Wiszniewski W, He F, Shaw C A, Yan J, et al. Oral curcumin mitigates the clinical and neuropathologic phenotype of the Trembler-J mouse: a potential therapy for inherited neuropathy. Am. J. Hum. Genet. 2007; 81: 438-453.

Liu, G.-M., Xu, K., Li, J., Luo, Y.-G., 2016. Curcumin upregulates S100 expression and improves regeneration of the sciatic nerve following its complete amputation in mice. Neural Regen. Res. 11, 1304-1311.

Lv, J., Cao, L., Zhang, R., Bai, F., Wei, P., 2018. A curcumin derivative J147 ameliorates diabetic peripheral neuropathy in streptozotocin (STZ)-induced DPN rat models through negative regulation AMPK on TRPA1. Acta Cir. Bras. 33, 533-541.

Mohammadi, R., Mahmoodi, H., 2013. Improvement of peripheral nerve regeneration following nerve repair by silicone tube filled with curcumin: a preliminary study in the rat model. Int. J. Surg. Lond. Engl. 11, 819-825.

Ndong Ntoutoume G M A, Granet R, Mbakidi J P, Brégier F, Léger D Y, Fidanzi-Dugas C, et al. Development of curcumin-cyclodextrin/cellulose nanocrystals complexes: New anticancer drug delivery systems. Bioorg. Med. Chem. Lett. 2016; 26: 941-945.

Ndong Ntoutoume G M A, Grassot V, Brégier F, Chabanais J, Petit J-M, Granet R, et al. PEI-cellulose nanocrystal hybrids as efficient siRNA delivery agents-Synthesis, physicochemical characterization and in vitro evaluation. Carbohydr. Polym. 2017; 164: 258-267.

Nobbio L, Vigo T, Abbruzzese M, Levi G, Brancolini C, Mantero S, et al. Impairment of PMP22 transgenic Schwann cells differentiation in culture: implications for Charcot-Marie-Tooth type 1A disease. Neurobiol. Dis. 2004; 16: 263-273.

Okamoto Y, Pehlivan D, Wiszniewski W, Beck C R, Snipes G J, Lupski J R, et al. Curcumin facilitates a transitory cellular stress response in Trembler-J mice. Hum. Mol. Genet. 2013; 22: 4698-4705.

Prasad, S., Tyagi, A. K., Aggarwal, B. B., 2014. Recent developments in delivery, bioavailability, absorption and metabolism of curcumin: the golden pigment from golden spice. Cancer Res. Treat. Off. J. Korean Cancer Assoc. 46, 2-18.

Sereda M, Griffiths I, Pühlhofer A, Stewart H, Rossner M J, Zimmerman F, et al. A transgenic rat model of Charcot-Marie-Tooth disease. Neuron 1996; 16: 1049-1060.

Sharma, R. A., Euden, S. A., Platton, S. L., Cooke, D. N., Shafayat, A., Hewitt, H. R., Marczylo, T. H., Morgan, B., Hemingway, D., Plummer, S. M., Pirmohamed, M., Gescher, A. J., Steward, W. P., 2004. Phase I clinical trial of oral curcumin: biomarkers of systemic activity and compliance. Clin. Cancer Res. Off. J. Am. Assoc. Cancer Res. 10, 6847-6854.

Shoba, G., Joy, D., Joseph, T., Majeed, M., Rajendran, R., Srinivas, P. S., 1998. Influence of piperine on the pharmacokinetics of curcumin in animals and human volunteers. Planta Med. 64, 353-356.

Wahlström, B. and Blennow, G., 1978. A study on the fate of Curcumin in the rat. Acta pharmacologica et toxicologica, Vol. 43, Issue 2, 86-92.

Yang, K.-Y., Lin, L.-C., Tseng, T.-Y., Wang, S.-C., Tsai, T.-H., 2007. Oral bioavailability of curcumin in rat and the herbal analysis from *Curcuma longa* by LC-MS/MS. J. Chromatogr. B Analyt. Technol. Biomed. Life. Sci. 853, 183-189.

The invention claimed is:

1. A method for treatment of a peripheral demyelinating neuropathy, comprising administering by injection to a subject in need thereof an effective dose of a complex comprising:

cellulose nanocrystals;

at least one β-cyclodextrin molecule; and at least one curcumin molecule, wherein the cellulose nanocrystals are loaded with β-cyclodextrin on their surfaces, and curcumin is included within β-cyclodextrin cavities on the cellulose nanocrystals, thereby forming a curcumin-β-cyclodextrin-cellulose nanocrystal complex, and administered at a curcumin equivalent dose of 0.2 mg/kg/day.

2. The method of claim 1, wherein the complex is administered in the form of a composition comprising the complex and at least one pharmaceutically acceptable excipient.

3. The method of claim 2, wherein the composition is in the form of a hydrogel.

4. The method of claim 2, wherein the composition is administered by injection by way of a subcutaneous, intramuscular, intravenous or perineural route.

5. The method of claim 2, wherein the peripheral demyelinating neuropathy is Charcot-Marie-Tooth disease.

6. The method of claim 2, wherein the peripheral demyelinating neuropathy is Charcot-Marie-Tooth disease type 1A.

7. The method of claim 2, wherein the peripheral demyelinating neuropathy is related to a traumatic injury.

8. A method for treatment of a peripheral demyelinating neuropathy, comprising administering by injection to a subject in need thereof an injectable pharmaceutical composition comprising a complex of cellulose nanocrystals, β-cyclodextrin, and curcumin, wherein the cellulose nanocrystals are loaded with β-cyclodextrin on their surfaces and curcumin is included within hydrophobic cavities of the β-cyclodextrin on the cellulose nanocrystals, thereby forming a curcumin-β-cyclodextrin-cellulose nanocrystal complex, and wherein the complex is administered at a curcumin-equivalent dose of 0.2 mg/kg/day by a route selected from subcutaneous, intramuscular, intravenous, or perineural injection, thereby improving motor nerve conduction velocity (MNCV) in the subject.

9. A method for treatment of Charcot-Marie-Tooth disease type 1A (CMT1A), comprising administering by injection to a subject in need thereof, an injectable pharmaceutical composition comprising a complex of cellulose nanocrystals, β-cyclodextrin, and curcumin, wherein the cellulose nanocrystals are loaded with β-cyclodextrin on their surfaces and curcumin is included within hydrophobic cavities of the β-cyclodextrin on the cellulose nanocrystals, thereby forming a curcumin-β-cyclodextrin-cellulose nanocrystal complex, and wherein the complex is administered at a curcumin-equivalent dose of 0.2 mg/kg/day, thereby maintaining measurable plasma curcumin at 8-12 hours post-dose and improving MNCV as assessed by electrophysiology.

* * * * *